Figure 1:
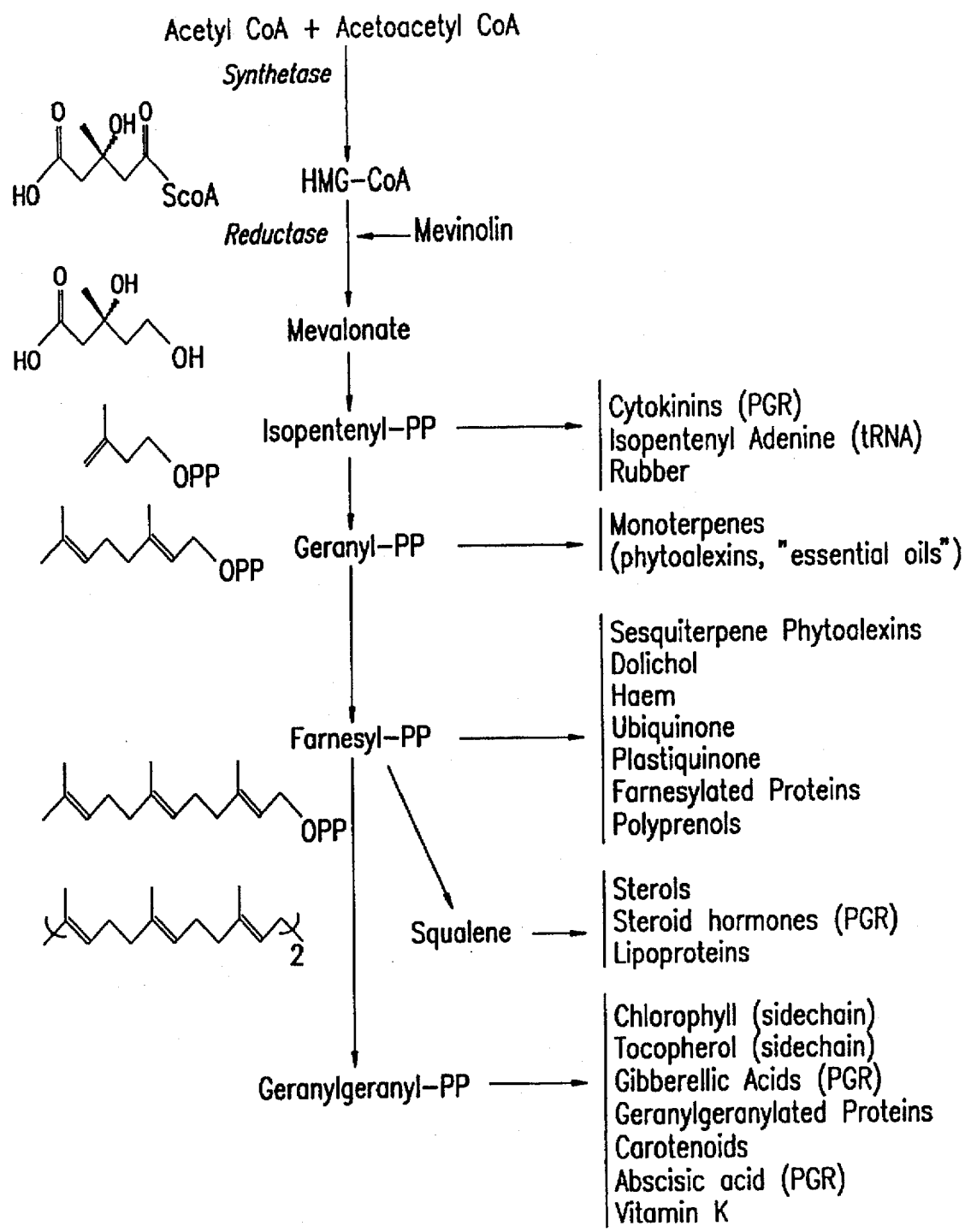

United States Patent [19]

Cramer et al.

[11] Patent Number: 5,689,056

[45] Date of Patent: Nov. 18, 1997

[54] HMG2 PROMOTER EXPRESSION SYSTEM

[75] Inventors: Carole Lyn Cramer; Deborah Louise Weissenborn, both of Blacksburg, Va.

[73] Assignee: Virginia Tech Intellectual Properties, Inc., Blacksburg, Va.

[21] Appl. No.: 550,544

[22] Filed: Nov. 7, 1995

Related U.S. Application Data

[63] Continuation of Ser. No. 100,816, Aug. 2, 1993, abandoned.

[51] Int. Cl.$^6$ .................... A01H 5/00; C12N 15/82; C12N 5/04

[52] U.S. Cl. .................. 800/205; 435/69.1; 435/70.1; 435/172.3; 435/240.4; 435/240.49; 435/320.1; 536/23.1; 536/24.1; 536/23.6

[58] Field of Search .................... 800/205; 435/69.1, 435/172.3, 240.4, 240.49, 320.1, 70.1; 536/24.1, 23.1, 23.6

[56] References Cited

PUBLICATIONS

Cramer C.L., et al., "Regulation of Defense–related Gene Expression during Plant–Pathogen Interactions" *Journal of Nematology*, 25:507–518 (1993).

Goddijn O.J.M., et al., "Differential gene expression in nematode–induced feeding structures of transgenic plant harbouring promoter–gusA fusion constructs" *The Plant Journal*, 4:863–873 (1993).

Opperman C.H., et al., "Root–Knot Nematode–Directed Expression of a Plant Root–Specific Gene" *Science*, 263:221–223 (1994).

Chappell et al., 1991, Plant Physiol. 96:127.
Choi et al., 1989, Phytopathology 79(10):1157.
Cramer et al., 1985, Science, 227:1240–42.
Cramer et al., 1991, J. Cell Biochem Suppl (15 Part A, p. 54).
Dixon et al., 1986, Philos Trans R Soc Lond B Biol Sci, 314:411–426.
Ji et al., 1992, Physiol. Plant, 84(2):185–192.
Park et al., 1989, Phytopathology 79(10):1198.
Park, Heesung (1990) Ph.D. Dissertation (complete), Virginia Polytechnic Institute and State University "Molecular Cloning, Characterization and Expression of 3–hydroxy–3–methylglutaryl CoenzymeA Reductase Gene From Tomato (*Lycopersicon esculentum*, Mill)".
Ryder et al., Organization, Structure and Activation of Plant Defense Genes, in *Biology and Molecular Biology of Plant Pathogen Interactions*, J.A. Bailey, ed., Springer–Verlag, (1986) pp. 207–219.
Yang et al., 1989, Phytopathology 79(10):1150–51.
Bhattacharyya et al., 1995, Plant Mol. Biol. 28:1–15.
Burnett et al., 1993, Plant Physiol. 103:41–48.
Enjuto et al., 1995, The Plant Cell 7:517–527.
Korth et al., 1993, Plant Physiol. 102(1 Suppl):71.
Nelson et al., 1994, Plant Mol. Biol. 25:401–412.
Stermer et al., 1992, Phytopathology 82:105.
Aoyagi et al., 1993, Plant Physiol. 102:622–638.

Bach et al., 1991, American Oil Chemists Society, Champaign, IL, pp. 29–49.
Bach et al., 1991, Lipids 26:637–648.
Brooker and Russell, 1975, Arch. Biochem. Biophys. 167:730–737.
Brooker and Russell, 1979, Arch. Biochem. Biophys. 198:323–334.
Caelles et al., 1989, Plant Mol. Biol. 13:627–638.
Chappell et al., 1991, Plant Physiol. 97:693–698.
Choi et al., 1992, Plant Cell 4:1333–1344.
Chye et al., 1991, Plant Mol. Biol. 16:567–577.
Chye et al., 1992, Plant Mol. Biol. 19:473–484.
Cramer et al., 1985, EMBO J. 4:285–289.
Cramer et al., 1989, J. Cell. Biochem. 13D:M408.
Dixon and Harrison, 1990, Adv. Genet. 28:165–234.
Genschik et al., 1992, Plant Mol. Biol. 20:337–341.
Learned and Fink, 1989, Proc. Natl. Acad. Sci. USA 86:2779–2783.
Maldonado–Mendoza et al., 1992, Plant Physiol. 100:1613–1614.
Narita and Gruissem, 1989, Plant Cell 1:181–190.
Narita et al., 1991, J. Cell. Biochem 15A:102(Abst).
Nelson et al., 1991, Abstract 1322, 3rd Intl. Cong. Intl. Soc. Plant Mol. Biol., Tucson, AZ.
Park et al., 1992, Plant Mol. Biol. 20:327–331.
Russell and Davidson, 1982, Biochem. Biophys. Res. Comm. 104:1537–1543.
Shih and Kuc, 1973, Phytopathology 63:826–829.
Stermer and Bostock, 1987, Plant Physiol. 84:404–408.
Stermer et al., 1991, Physiol. Mol. Plant Pathol. 39:135–145.
Stermer et al., 1992, Phytopathology 82:1085.

(List continued on next page.)

*Primary Examiner*—Elizabeth McElwain
*Attorney, Agent, or Firm*—Pennie & Edmonds LLP

[57] ABSTRACT

The promoter elements of plant HMG2 HMGR genes are described. The HMG2 promoter elements are responsive to pathogen-infection, pest-infestation, wounding, or elicitor or chemical treatments. The HMG2 elements are also active in specialized tissues of the plant including pollen and mature fruits. HMG2 promoter elements and HMG2-derived promoters can be advantageously used to drive the expression of disease and pest resistance genes, whereby transgenic plants having such gene constructs would be resistant to the targeted disease and pest. In particular, the HMG2 gene expression system can be utilized in developing nematode-resistant plants. HMG2 promoter elements and HMG2-derived promoters can also be advantageously used to drive the post-harvest expression of desired gene products in plants, wherein the expression of the desired gene product is deferred until the expression is induced by mechanical wounding and/or elicitor treatment of all plant tissue shortly before, during or shortly after harvesting the plant. Further, HMG2 promoter elements and HMG2-derived promoters can also be advantageously used to drive the expression of desired gene products in plant cell cultures, wherein the expression of the desired gene product is deferred until the expression is induced by mechanical wounding or elicitor treatment.

30 Claims, 18 Drawing Sheets

OTHER PUBLICATIONS

Wong et al., 1982, Arch. Biochem. Biophys. 216:631–638.
Yang et al., 1989, Mol. Plant–Microb. Interact. 2:195–201.
Yang et al., 1991, Plant Cell 3:397–405.
Barton et al (1987) Plant Physiol 85:1103–1109.
Larkins et al (1985) J Cell Biochem Suppl. 0 (9 Part C):264.
Casacuberta et al (1991) Plant Mol Biol 16:527–536.
Williams et al (1992, May) Bio/Technology 10:540–543.
Leah et al (1991) J. Mol Biol 266(3):1564–1573.

```
                                                                            HMG2
     -62  AAAGTCCAGCGCGGCAACCGGGTTC...CTCTATAAATACATTTCCTACAT
                ||| |||||||||||||||||     |||||||||||| |||| ||
     -56  AAATTGTAGCGCGGCCAACCGCTTTCACTCTATAAATACGTTTCTTCTAC   HMG1
                              +1-->
     -14  CTTCTCTTCTCCTCCATCACTCTCTTTAACAATTATACTTGT
          ||  |||  |||   |||||||||  || || ||| |||| |
      -6  TTTCGCTTCCCCACACAACCATTGCTTAATACACATTGACTTTCT
                +1-->
     +37  CAATCATCAATCCCACAAACAACACTTTTCTCCTCTTTTC.....CT
                ||||  ||  ||||||||||||                ||
     +44  C.....TCTCTCTCA..............TTTCTCTTTTTTTTCTTTTCA
                                                          .
     +83  CACCGGGCGGCAGACTTACCGGTGAA............AAAATGGACGTTC
           ||||| ||||||  |||  ||| ||            |||||||||||
     +77  AAAGCCGGTGTTCCTGCCGGAAAATCAACTAAATTACAATGGACGTTC
                                                    .
     121  GCCGGAGATCTGAAGAGCCTGTTTATCCATCTAAGGTCTTTGCCGCCGAT
           |||| || ||  ||||||||| ||||||| ||| ||||| ||||| |
     127  GCCGGCGACCAGTTAAGCCTTTATGCACATCAAAAGATGCTTCCGCCGGC
                                                    .
     171  GAAAAACCTCTCAAACCCCAAGAAACAACAACAACAAGAGGACAA....
                 ||||                   |||||||||||
     177  G....AACCTCT.................GAAACAACAACAA......
```

FIG. 2A

```
                                                           . . . . . membrane
                                                                     domain
                                                                     of
                                                           . . . . . protein 221  GAATACCCTTCTCAT..TGATGCTTCCGATGCTCTCCCACTTCCTTTGTA
     ---------------  ----------------------------------
198  .......GTTTCTAGTCCTAAAGCATCCGACGCGCTTCCACTCCCATTGtA
                      ---------------------------------
269  TCTCACGACGAATGGGCTTGTTTTCACCATGTTTTTCTCTGTTATGTATT
     ---------------- ---------------------------------
242  CCT...AACCAATGGGTTGTTtTCACCATGTTTTTCTCTGTTATGTATT
        ----------- ------------------------------------
319  TTCTTCTATCAAGGTGGCGTGAGAAATCAGGAATTCCACTCCCTTTACAT
     -------------  ----------------------------------
289  TTCTTCTCGTAAGGTGGCGTGAGAAGATCCGTAATTCTATTCCTCTCAT
     ------------  ----------------------------------
369  GTCGTTACGCTTTCTGAATTGGGTGCTATTGTTTCGTTAATTGCTTCTGT
     ---------------------------------  ---------------
339  GTGGTTACCCTTTCTCTGAATTGTTAGCTATGGTGTCATTGATTGCTTCCGT
     ---------------  ---------------------------------
419  CATTTATCTTCTTGGTTTCTTGGGTTTGTTCAGACGTTTGTGT
     -----------------------------------------
389  TATATATCTATTGGGTTCTTTGGGATTGGGTTTGTTCAGTCGTTTGTGT
     ----------------------------------------------
```

FIG. 2B

```
                                                                    HMG2  HMG1
469  CAAGGGGAAATAATGATTCATG..........GGATGAAAAATGATGAGGAA
         ||| |||  ||| ||||||          ||||||| ||||||| ||
439  CCAGGTCGAATAGTGATTCATGGGATATTGAGGATGAGAATGCTGAGCAG

510  TTTCTATTGAAGGAAGATAGTCG.........TTGTGGGCCTGCAACTAC
         ||||||| |||||||| |||              ||||||||||||||
489  CTAATTATCGAGGAAGATAGCCGCGGGACCATGTGCTGCTGCAACTAC

551  TCTTGGTTGTGCTGTTCCTGCACCACCCTGCTCGACAAATTGCCCCAATGG
         |||||  |||||| ||||  ||||||||| |||||  |||||||||||||
539  TCTTGGCTGCGTTGTGCCTGCCTCCACCTGTTCGAAAAATTGCCCCAATGG

601  CACCACCCTCAACCT.........TCTATGTCTATGGTAGAGAAACCTGCA
         ||||| |||||||             |||| ||||  |||||||| |||
589  TTCCACAGCAACCTGCCAAGGCAGCTTGTCCCAACGGAAGAGAAGCCTGCG

642  CCGTTGATAACATCAGCTTCGTTCTGGGAAGACGAAGAGAGATAATTAAATC
         |||||||| | |||||| ||| ||||||||| ||||| |||||| ||||||
639  CCAATAATTATGCCAGCATTATCGGAAGATGACGAGGAGATAATACAATC
```

FIG.2C

```
                                                                  . . . . . catalytic
                                                                            domain of
                                                                            protein . . . >

692  CGTGGTGCAGGGGGAAAATACCATCATACTCATTGGAATCCAAGCTCGGTG
     |||||||||||||   ||||| ||||||||| |||||||||| ||||||||
689  TGTTGTTCAGGGTAAAACACCATCATATTCTTTGGAATCAAAGCTTGGTG

742  ATTGTAAGCGCGCTGCTTCGATAAGGAAAGAGGTGATGCAGAGGATTACA
     ||||| ||| | |||||||||| |||||||||| ||| ||||||| |||
739  ATTGTATGAGAGCTGCTTCGATTCGAAAAGAGAGGCGTTACAGAGGATCACA

792  GGGAAGTCTCTAGAAGGGCTACCATTGGAAGGATTTAACTATGAATCTAT
     ||||||||| | |||||| |||||||||||||| |||| ||||||| |||
789  GGGAAGTCATTGGAAGGGCTCCCATTGGAAGGATTTGACTATGAGTCTAT

842  TCTTGGGCAGTGTTGTGAGATGCCAATTGGCTACGTGCAGATACCAGTGG
     ||||||||| |||||||| |||||| |||||| |||| ||| |||| ||
839  TCTTGGACAATGCTGTGTGAGATGCCCTGTAGGATATGTGCAAATACCGGTTG

892  GAATAGCAGGGCCATTGTTGCTTAACGGAAAAGGAGTTTTCGGTGCCCATG
     |||| ||||||||| ||||||| ||  |||| ||||||| |||||||||||
889  GTATTGCAGGGCCCTTTGTTGCTTGATGGGAGAGAGTACTCAGTGCCAATG
```

FIG. 2D

```
942  GCAACCCACAGAAGGATGTTTAGTGGCTAGCACCAACAGAGGTTGCAAGGC
     ||||| ||||||||||| ||||||||||||||| |||||||| ||||||||
939  GCAACTACAGAAGGGTGTTTAGTTGCTAGCACCAACAGGGGTTGCAAGGC

992  TATCTATGCTCTGGTGGTGCTACATGCATTTTGCTTCGTGATGGTATGA
     |||||  ||||||||||    ||| ||||||||||||| |||||| ||||
989  TATCTTTGTCTCTGGTGGCGCCAACAGCATTTTGCTCAGAGATGGCATGA

1042 CCAGAGCACCATGTCTGTCAGGTTCGGCACAGCCAAAGGGCAGCAGAGTTG
      || || ||| |||||| |||||| ||   |||| |||| |||||||||||
1039 CAAGAGCTCCGGTTGTCCGGTTCACCACCGCCAAAAGAGCCGCAGAGTTG

1092 AAGTTCTTTGTTGAAGATCCCCATAAAATTTGAGTCACTTGCTAACGTTT
     || |||| || |||||||||||  ||| ||||||| |||| || | |||
1089 AAATTCTTCGTTGAGGATCCCCTTAACTTTGAGATTCTTTCCCTTATGTT

1142 CAACCAGTAAGT end of Intron I
     ||| ||||| ||
1139 CAACAAGTGAGT end of Intron I
```

FIG. 2E

```
-1036  AAATTgCTGA GATACCTCCT TTGTCTTTTT TCCACTGTGG TCTCAGTTGA
 -986  CTATAAGAAA TGTTGCTAAC TATTTTAAT  GTCCAAACCT CAAATATCAA
 -936  GCCATGCAAA ATTAACCATT TTCTTAACGT GGATATATAC CTATTCCACC
 -886  ACATGGTACC CTATTCCAAC TATATTAAAA AAAATAAAAT ACTCTAGTTA
       primer 22
 -836  ATATTGATCA AAATTTATAT AATTACATC  TCAATAATAT AAAAAGTTAT
 -786  TGCATGCGTA CTTATGAAAT TTGTAGGTTT TAAAATTGTG TAGGGCTGGG
 -736  CATAGAAAAT TGAATTATCA GATCGGATGG ACAGTTTTTT GGTATTTGGT
 -686  ATTCGGTAAT TAAGTATTTA ATATGATATT TGGAAGTACA ATTTTAGAAT
 -636  CATAATATTC TGAGTTTGGT ATGAAATATT AGTACCATTT AATATTTTTC
 -586  GTATACCGAA TTATTTATGA AGGCATGTAT CGACATGTCC ATTATTCATT
 -536  AGTACAAATT TAAAGAGAAA GTTAAAAGAA TAAATATAAA AAATGTAAAT
 -486  ACATGTCTTT TAGTTGTATC AATTATTTT  TCTTGATATC TTTTTATTTA
```

FIG. 4A

```
-436  TTAATTTTTT TAAATTGTAC CCTGCATAAA AGAAATAGA  AATAATTGGA
-386  AAAAAAGTAT TATTTTTATA ATACAATCCG ATATAATTAC AATACGATAT
                                                  primer 20
-336  TACCGAATAT TATACTAAAT CAAAATTTTA TTTATCATAT CAAATTATTA
-286  AACTGATATT TCAAATTTTA ATATTTAATA TCTACTTTCA ACTATTATTA
-236  CCTAATTATC AAATGCAAAA TGTATGAGTT ATTTCATAAT AGCCCAGTTC
-186  GTATCCAAAT ATTTTACACT TGACCAGTCA ACTTGACTAT ATAAAACTTT
-136  ACTTCAAAAA ATTAAAAAAA AAAGAAAGTA TATTATTGTA AAAGATAATA
 -86  CTCCATTCAA AATATAAAAT GAAAAAAGTC CAGGCGGGCA ACCGGGTTCC
                                          primer 19
                                                 +1 --->
 -36  TCTATAAATA CATTTCCTAC ATCTTCTCTT CTCCCTCACAT CCCATCACTC
 +15  TTCTTTTAAC AATTATACTT GTCAATCATC AATCCCACAA ACAACACTTT
 +65  TTCTCTCCTC TTTTTCCTCA CCGGCGGGCAG ACTTACCGGT GAAAAATGG
+115  ACGTTCGCCG GAGATCTGAA GAGCCTGTTT ATCCATCTAA GGTCTTTGCC
      primer 18  BglII
```

FIG. 4B

+165 GCCGATGAAA AACCTCTCAA ACCCCACAAG AAACAACAAC AACAACAAGA
+215 GGACAAGAAT ACCCTTCTCA TTGATGCTTC CGATGCTCTC CCACTTCCTT
+265 TGTATCTCAC GAATGGCTTG TTTTTCACCA TGTTTTTCTC TGTTATGTAT
+315 TTTCTTCTAT CAAGGTGGCG TGAGAAAATC AGGAATTC
                                     ‾‾‾‾‾‾‾‾
                                       EcoRI

FIG. 4C

```
  1  CGAATCAACT AGTTATACTC TCTCACTTAT TTTGTATTT  GTACACCTTT
 51  GTCTTACGTG GTGCATTCTG TGTTACTCGA TTGAGGCGCA TGCGAGATAT
101  TTGGATGCCA AGCCTAAGTC AAAAGGTGC  AGAAAATTAC AAAAAAAAT
151  AAAATTCAGA GxGTAATAGG ACGTTAGTTT ATTTAAAGTG TGTTTTAAA
201  ATTCAATTA  TAATCTACAA AGATACTTCT GCATTATATA TATATATA
251  TATATATATA TATATATATA TATATATATA TATATATATA TATATATATA
301  TAAAAGAAG  ACAGGTACAT TGGATTTTAG CTTGTTTGGT GTCCCAGCAA
351  ACAGCxAAGG AGTAGTATTT TAATTAATAA GTAATCAATT TTGGGTGAGA
401  AATTGCTGAG ATACCTCCTT TGTCTTTTTT TTATATATAT ATATATATAT
451  ATATATATAT ATATATATTA
```

FIG.5

```
      EcoRI
  1   GAATTCGAAG CAACTTtCCT GACTTGTTTG GTCATGCTTA TAGGTTCACC
 51   CAGACTTCGC AGCTCATTTG TAATGGAAGA CAACTTTGTG AACATGTCAT
101   GTATAGTTTC TCCTTCCTTC CTTCATTTTG AAGTTCTCAT ATCGTGAGGT
151   GAGCATGTCa atcTTGGATT CTTGACTTG  TTCAGTTTCT TCATGTGTAG
201   TCAACAAGCA ATCCCAGATT TCTTTAGCAG ACTCACAGGC TGACACTCTA
251   TTGTACTCAT CAGGTCCTAT CCCACAGACC ATAAGAGTTT TACCTTTGAA
301   GCCCTTTtCT ATCTTTTtcc TGTCAGCATC ATCATATTTC TGCTTGGGCT
351   TTGGAaCAGT GATGGTCTTT CTCATCTTtA CTTCATCATT GGACAAGAGT
401   CACTAGTATA ATATCCCATA ACTCGCTATC TTCAGCCATA ATCGTGCATT
451   CTAACTTTCC ACCAACTGTA GAAATGTCCA tTCAAACGAG GAGGTCTATG
501   TGATGACTGA CCTTC
```

FIG. 6

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1212 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:1:

```
AAAGTCCAGC   GCGGCAACCG   GGTTCCTCTA   TAAATACATT   TCCTACATCT   TCTCTTCTCC        60

TCACATCCCA   TCACTCTTCT   TTTAACAATT   ATACTTGTCA   ATCATCAATC   CCACAAACAA       120

CACTTTTTCT   CTCCTCTTTT   TCCTCACCGG   CGGCAGACTT   ACCGGTGAAA   AAATGGACGT       180

TCGCCGGAGA   TCTGAAGAGC   CTGTTATCC   ATCTAAGGTC   TTTGCCGCCG   ATGAAAAACC       240

TCTCAAACCC   CACAAGAAAC   AACAACAACA   ACAAGAGGAC   AAGAATACCC   TTCTCATTGA       300

TGCTTCCGAT   GCTCTCCAC   TTCCTTTGTA   TCTCACGAAT   GGCTTGTTTT   TCACCATGTT       360

TTTCTCTGTT   ATGTATTTC   TTCTATCAAG   GTGGCGTGAG   AAAATCAGGA   ATTCCACTCC       420

TTTACATGTC   GTTACGCTTT   CTGAATTGGG   TGCTATTGTT   TCGTTAATTG   CTTCTGTCAT       480

TTATCTTCTT   GGTTTCTTTG   GGATTGGGTT   TGTTCAGACG   TTTGTGTCAA   GGGGAAATAA       540

TGATTCATGG   GATGAAAATG   ATGAGGAATT   TCTATTGAAG   GAAGATAGTC   GTTGTGGGCC       600
```

-continued

| | | | | | | |
|---|---|---|---|---|---|---|
| TGCAACTACT | CTTGGTTGTG | CTGTTCCTGC | ACCACCTGCT | CGACAAATTG | CCCCAATGGC | 660 |
| ACCACCTCAA | CCTTCTATGT | CTATGGTAGA | GAAACCTGCA | CCGTTGATAA | CATCAGCTTC | 720 |
| GTCTGGGGAA | GACGAAGAGA | TAATTAAATC | CGTGGTGCAG | GGGAAAATAC | CATCATACTC | 780 |
| ATTGGAATCC | AAGCTCGGTG | ATTGTAAGCG | CGCTGCTTCG | ATAAGGAAAG | AGGTGATGCA | 840 |
| GAGGATTACA | GGGAAGTCTC | TAGAAGGGCT | ACCATTGGAA | GGATTTAACT | ATGAATCTAT | 900 |
| TCTTGGGCAG | TGTTGTGAGA | TGCCAATTGG | GTACGTGCAG | ATACCAGTGG | GAATAGCAGG | 960 |
| GCCATTGTTG | CTTAACGGAA | AGGAGTTTTC | GGTGCCCATG | GCAACCACAG | AAGGATGTTT | 1020 |
| AGTGGCTAGC | ACCAACAGAG | GTTGCAAGGC | TATCTATGCT | TCTGGTGGTG | CTACATGCAT | 1080 |
| TTTGCTTCGT | GATGGTATGA | CCAGAGCACC | ATGTGTCAGG | TTCGGCACAG | CCAAAAGGGC | 1140 |
| AGCAGAGTTG | AAGTTCTTTG | TTGAAGATCC | CATAAAATTT | GAGTCACTTG | CTAACGTTTT | 1200 |
| CAACCAGTAA | GT | | | | | 1212 |

( 2 ) INFORMATION FOR SEQ ID NO:2:

( i ) SEQUENCE CHARACTERISTICS:
        ( A ) LENGTH: 1207 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:2:

| | | | | | | |
|---|---|---|---|---|---|---|
| AAATTGTAGC | GCGCCAACCG | CTTTTCACTC | TATAAATACG | TTTCTTCTAC | TTTCGCTTCC | 60 |
| CCACACAAAC | CATCACTGCT | TAATACACAT | TTGACTTTCT | CTCTCTCTCA | TTTCTCTTTT | 120 |
| TTTTTTCTTT | TCAAAAAGCC | GGTGTTCCTG | CCGGAAAATC | AACTAAATTT | ACAATGGACG | 180 |
| TTCGCCGGCG | ACCAGTTAAG | CCTTTATGCA | CATCAAAAGA | TGCTTCCGCC | GGCGAACCTC | 240 |
| TGAAACAACA | ACAAGTTTCT | AGTCCTAAAG | CATCCGACGC | GCTTCCACTC | CCATTGTACC | 300 |
| TAACCAATGG | GTTGTTTTC | ACCATGTTTT | TCTCTGTTAT | GTATTTCTT | CTCGTAAGGT | 360 |
| GGCGTGAGAA | GATCCGTAAT | TCTATTCCTC | TTCATGTGGT | TACCCTTTCT | GAATTGTTAG | 420 |
| CTATGGTGTC | ATTGATTGCT | TCCGTTATAT | ATCTATTGGG | TTTCTTTGGG | ATTGGGTTTG | 480 |
| TTCAGTCGTT | TGTGTCCAGG | TCGAATAGTG | ATTCATGGGA | TATTGAGGAT | GAGAATGCTG | 540 |
| AGCAGCTAAT | TATCGAGGAA | GATAGCCGCC | GGGGACCATG | TGCTGCTGCA | ACTACTCTTG | 600 |
| GCTGCGTTGT | GCCTCCACCA | CCTGTTCGAA | AAATTGCCCC | AATGGTTCCA | CAGCAACCTG | 660 |
| CCAAGGCAGC | TTTGTCCCAA | ACGGAGAAGC | CTGCGCCAAT | AATTATGCCA | GCATTATCGG | 720 |
| AAGATGACGA | GGAGATAATA | CAATCTGTTG | TTCAGGGTAA | AACACCATCA | TATTCTTTGG | 780 |
| AATCAAAGCT | TGGTGATTGT | ATGAGAGCTG | CTTCGATTCG | AAAAGAGGCG | TTACAGAGGA | 840 |
| TCACAGGGAA | GTCATTGGAA | GGGCTCCCAT | GGAAGGATT | TGACTATGAG | TCTATTCTTG | 900 |
| GACAATGCTG | TGAGATGCCT | GTAGGATATG | TGCAAATACC | GGTTGGTATT | GCAGGGCCTT | 960 |
| TGTTGCTTGA | TGGGAGAGAG | TACTCAGTGC | CAATGGCAAC | TACAGAAGGG | TGTTTAGTTG | 1020 |
| CTAGCACCAA | CAGGGGTTGC | AAGGCTATCT | TTGTCTCTGG | TGGCGCCAAC | AGCATTTTGC | 1080 |
| TCAGAGATGG | CATGACAAGA | GCTCCGGTTG | TCCGGTTCAC | CACCGCCAAA | AGAGCCGCAG | 1140 |
| AGTTGAAATT | CTTCGTTGAG | GATCCCCTTA | ACTTTGAGAT | TCTTTCCCTT | ATGTTCAACA | 1200 |
| AGTGAGT | | | | | | 1207 |

( 2 ) INFORMATION FOR SEQ ID NO:3:

5,689,056

37                                                                         38
-continued ( i ) SEQUENCE CHARACTERISTICS:
    ( A ) LENGTH: 1388 base pairs
    ( B ) TYPE: nucleic acid
    ( C ) STRANDEDNESS: double
    ( D ) TOPOLOGY: unknown ( i i ) MOLECULE TYPE: DNA (genomic)

( x i ) SEQUENCE DESCRIPTION: SEQ ID NO:3:

| AAATTGCTGA | GATACCTCCT | TTGTCTTTTT | TCCACTGTGG | TCTCAGTTGA | CTATAAGAAA | 60 |
| TGTTGCTAAC | TATTTTTAAT | GTCCAAACCT | CAAATATCAA | GCCATGCAAA | ATTAACCATT | 120 |
| TTCTTAACGT | GGATATATAC | CTATTCCACC | ACATGGTACC | CTATTCCAAC | TATATTAAAA | 180 |
| AAAATAAAAT | ACTCTAGTTA | ATATTGATCA | AAATTTATAT | AATTTACATC | TCAATAATAT | 240 |
| AAAAGTTAT | TGCATGCGTA | CTTATGAAAT | TTGTAGGTTT | TAAAATTGTG | TAGGGCTGGG | 300 |
| CATAGAAAAT | TGAATTATCA | GATCGGATGG | ACAGTTTTT | GGTATTTGGT | ATTCGGTAAT | 360 |
| TAAGTATTTA | ATATGATATT | TGGAAGTACA | ATTTTAGAAT | CATAATATTC | TGAGTTTGGT | 420 |
| ATGAAATATT | AGTACCATTT | AATATTTTC | GTATACCGAA | TTATTTATGA | AGGCATGTAT | 480 |
| CGACATGTCC | ATTATTCATT | AGTACAAATT | TAAAGAGAAA | GTTAAAAGAA | TAAATATAAA | 540 |
| AAATGTAAAT | ACATGTCTTT | TAGTTGTATC | AATTTATTTT | TCTTGATATC | TTTTTATTTA | 600 |
| TTAATTTTTT | TAAATTGTAC | CCTGCATAAA | AGAAAATAGA | ATAATTGGA | AAAAAAGTAT | 660 |
| TATTTTTATA | ATACAATCCG | ATATAATTAC | AATACGATAT | TACCGAATAT | TATACTAAAT | 720 |
| CAAATTTAA | TTTATCATAT | CAAATTATTA | AACTGATATT | TCAAATTTTA | ATATTTAATA | 780 |
| TCTACTTTCA | ACTATTATTA | CCTAATTATC | AAATGCAAAA | TGTATGAGTT | ATTTCATAAT | 840 |
| AGCCCAGTTC | GTATCCAAAT | ATTTTACACT | TGACCAGTCA | ACTTGACTAT | ATAAAACTTT | 900 |
| ACTTCAAAAA | ATTAAAAAAA | AAGAAAGTA | TATTATTGTA | AAAGATAATA | CTCCATTCAA | 960 |
| AATATAAAAT | GAAAAAGTC | CAGCGCGGCA | ACCGGGTTCC | TCTATAAATA | CATTTCCTAC | 1020 |
| ATCTTCTCTT | CTCCTCACAT | CCCATCACTC | TTCTTTTAAC | AATTATACTT | GTCAATCATC | 1080 |
| AATCCACAA | ACAACACTTT | TTCTCTCCTC | TTTTTCCTCA | CCGGCGGCAG | ACTTACCGGT | 1140 |
| GAAAAAATGG | ACGTTCGCCG | GAGATCTGAA | GAGCCTGTTT | ATCCATCTAA | GGTCTTTGCC | 1200 |
| GCCGATGAAA | AACCTCTCAA | ACCCCACAAG | AAACAACAAC | AACAACAAGA | GGACAAGAAT | 1260 |
| ACCCTTCTCA | TTGATGCTTC | CGATGCTCTC | CCACTTCCTT | TGTATCTCAC | GAATGGCTTG | 1320 |
| TTTTTCACCA | TGTTTTTCTC | TGTTATGTAT | TTTCTTCTAT | CAAGGTGGCG | TGAGAAAATC | 1380 |
| AGGAATTC | | | | | | 1388 |

( 2 ) INFORMATION FOR SEQ ID NO:4:

( i ) SEQUENCE CHARACTERISTICS:
        ( A ) LENGTH: 480 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: modified_base
        ( B ) LOCATION: 162
        ( D ) OTHER INFORMATION: /label=n
            / note="n=x=Unknown nucleotide"

( i x ) FEATURE:
        ( A ) NAME/KEY: modified_base
        ( B ) LOCATION: 356
        ( D ) OTHER INFORMATION: /label=n
            / note="n=x=Unknown nucleotide"

(x i) SEQUENCE DESCRIPTION: SEQ ID NO:4:

```
CGAATCAACT  AGTTATACTC  TCTCACTTAT  TTTTGTATTT  GTACACCTTT  GTCTTACGTG      60

GTGCATTCTG  TGTTACTCGA  TTGAGGCGCA  TGCGAGATAT  TTGGATGCCA  AGCCTAAGTC     120

AAAAAGGTGC  AGAAATTAC   AAAAAAAAAT  AAAATTCAGA  GNGTAATAGG  ACGTTAGTTT     180

ATTTAAAGTG  TGTTTTAAA   ATTTCAATTA  TAATCTACAA  AGATACTTCT  GCATTATATA     240

TATATATATA  TATATATATA  TATATATATA  TATATATATA  TATATATATA  TATATATATA     300

TAAAAAGAAG  ACAGGTACAT  TGGATTTTAG  CTTGTTTGGT  GTCCAGCAA   ACAGCNAAGG     360

AGTAGTATTT  TAATTAATAA  GTAATCAATT  TTGGGTGAGA  AATTGCTGAG  ATACCTCCTT     420

TGTCTTTTTT  TTATATATAT  ATATATATAT  ATATATATAT  ATATATATAT  ATATATATTA     480
```

(2) INFORMATION FOR SEQ ID NO:5:

(i) SEQUENCE CHARACTERISTICS:
        (A) LENGTH: 515 base pairs
        (B) TYPE: nucleic acid
        (C) STRANDEDNESS: double
        (D) TOPOLOGY: unknown (i i) MOLECULE TYPE: DNA (genomic)

(x i) SEQUENCE DESCRIPTION: SEQ ID NO:5:

```
GAATTCGAAG  CAACTTTCCT  GACTTGTTTG  GTCATGCTTA  TAGGTTCACC  CAGACTTCGC      60

AGCTCATTTG  TAATGGAAGA  CAACTTTGTG  AACATGTCAT  GTATAGTTTC  TCCTTCCTTC     120

CTTCATTTTG  AAGTTCTCAT  ATCGTGAGGT  GAGCATGTCA  ATCTTGGATT  CTTTGACTTG     180

TTCAGTTTCT  TCATGTGTAG  TCAACAAGCA  ATCCCAGATT  TCTTTAGCAG  ACTCACAGGC     240

TGACACTCTA  TTGTACTCAT  CAGGTCCTAT  CCCACAGACC  ATAAGAGTTT  TACCTTTGAA     300

GCCCTTTTCT  ATCTTTTTCC  TGTCAGCATC  ATCATATTTC  TGCTTGGGCT  TTGGAACAGT     360

GATGGTCTTT  CTCATCTTTA  CTTCATCATT  GGACAAGAGT  CACTAGTATA  ATATCCCATA     420

ACTCGCTATC  TTCAGCCATA  ATCGTGCATT  CTAACTTTCC  ACCAACTGTA  GAAATGTCCA     480

TTCAAACGAG  GAGGTCTATG  TGATGACTGA  CCTTC                                  515
```

HMG2 PROMOTER EXPRESSION SYSTEM

This is a continuation, of application Ser. No. 08/100,816 filed Aug. 2, 1993, now abandoned.

TABLE OF CONTENTS
1. INTRODUCTION
2. BACKGROUND OF THE INVENTION
   - 2.1. PLANT DEFENSE RESPONSES
   - 2.2. PHYSIOLOGICAL ROLES OF HMGR IN PLANTS
   - 2.3. PLANT HMGR GENES
   - 2.4. TOMATO HMGR GENES
   - 2.5 THE FUNCTIONS AND EXPRESSION PATTERNS OF DIFFERENT HMGR GENES
   - 2.6. PLANT HMGR PROMOTERS
3. SUMMARY OF THE INVENTION
   - 3.1. DEFINITIONS
4. DESCRIPTION OF THE FIGURES
5. DESCRIPTION OF THE INVENTION
   - 5.1 HMG2 PROMOTERS
   - 5.2 CIS-REGULATORY ELEMENTS OF HMG2 PROMOTERS
   - 5.3 HMG2 PROMOTER-DRIVEN GENE CONSTRUCTS
   - 5.4 RECOMBINANT DNA CONSTRUCTS
   - 5.5 PRODUCTION OF TRANSGENIC PLANTS AND PLANT CELLS
   - 5.6 SELECTION AND IDENTIFICATION TRANSFORMED PLANTS AND PLANT CELLS
   - 5.7 EXPRESSION OF HETEROLOGOUS GENE PRODUCTS IN TRANSGENIC PLANTS
6.0 EXAMPLE: ISOLATION AND CHARACTERIZATION OF THE TOMATO HMG2 PROMOTER AND HMG2 GENE FUSIONS
   - 6.1 MATERIALS AND METHODS
     - 6.1.1 PLANT AND FUNGAL MATERIAL
     - 6.1.2 GENOMIC LIBRARY SCREENING
     - 6.1.3 NUCLEIC ACID ISOLATION
     - 6.1.4 HYBRIDIZATION ANALYSIS
     - 6.1.5 HMG2 PROMOTER:REPORTER GENE FUSIONS
     - 6.1.6 SEQUENCING OF HMG2 PROMOTER DELETIONS
     - 6.1.7 GUS GENE FUSIONS WITH HMG2 PROMOTER DELETIONS
     - 6.1.8 TRANSFORMATION OF GENE CONSTRUCTS INTO PLANTS
     - 6.1.9 EXAMINATION OF GUS EXPRESSION IN TRANSGENIC PLANTS
     - 6.1.10 BACTERIAL INFECTION INDUCTION OF HMG2 PROMOTER ACTIVITY
     - 6.1.11 FUNGAL INFECTION INDUCTION OF HMG2 PROMOTER ACTIVITY
     - 6.1.12 NEMATODE INFESTATION INDUCTION OF HMG2 PROMOTER ACTIVITY
     - 6.1.13 POST-HARVEST WOUND INDUCTION OF HMG2 PROMOTER ACTIVITY
     - 6.1.14 FIELD PERFORMANCE OF TRANSGENIC PLANTS CONTAINING HMG2:GUS GENE FUSIONS
   - 6.2 RESULTS
     - 6.2.1 HMG2 PROMOTER ACTIVITY
     - 6.2.2 TISSUE SPECIFIC ACTIVITY OF THE HMG2 PROMOTER
     - 6.2.3 DEFENSE-RELATED ACTIVITY OF THE HMG2 PROMOTER
     - 6.2.4 NEMATODE ACTIVATION OF THE HMG2 PROMOTER
     - 6.2.5 ACTIVATION OF THE HMG2 PROMOTER BY NATURAL PREDATORS
     - 6.2.6 DISSECTION OF HMG2 PROMOTER
     - 6.2.7 HMG2 CIS-REGULATORY ELEMENTS
     - 6.2.8 POST-HARVEST INDUCTION OF HMG2 PROMOTER
     - 6.2.9. USE OF HMG2 PROMOTER FOR DEVELOPING NEMATODE RESISTANT PLANTS
7. DEPOSIT OF MICROORGANISM

1. INTRODUCTION

The present invention relates to HMG2 promoters, active fragments thereof, and their use to drive the expression of heterologous genes. Expression vectors may be constructed by ligating a DNA sequence encoding a heterologous gene to a HMG2 promoter or a promoter modified with a HMG2 cis-regulatory element. Such constructs can be used for the expression of proteins and RNAs in plant cell expression systems in response to elicitor or chemical induction, or in plants in response to wounding, pathogen infection, pest infestation as well as elicitor or chemical induction.

2. BACKGROUND OF THE INVENTION

Plant diseases caused by fungal, bacterial, viral and nematode pathogens cause significant damage and crop loss in the United States and throughout the world. Current approaches to disease control include breeding for disease resistance, application of chemical pesticides, and disease management practices such as crop rotations. Recent advances in plant biotechnology have led to the development of transgenic plants engineered for enhanced resistance to plant pests and pathogens. These successes indicate that biotechnology may significantly impact production agriculture in the future, leading to improved crops displaying genetic resistance. This mechanism of enhanced disease resistance has the potential to lower production costs and positively impact the environment by reducing the use of agrichemicals. Key to the effective application of plant biotechnology to agricultural productivity is 1) an understanding of the molecular basis of disease resistance and plant-pathogen interaction and 2) the identification of the necessary molecular tools and defense genes required for engineering resistance.

2.1. PLANT DEFENSE RESPONSES

Higher plants have evolved a variety of structural and chemical weapons for protection against pathogens, predators, and environmental stresses. Expression of resistance toward pathogens and pests involves the rapid induction of genes leading to accumulation of specific defense-related compounds (Dixon et al., 1990, Adv. Genet. 28:165–234). These responses include accumulation of phytoalexin antibiotics, deposition of lignin-like material, accumulation of hydroxyproline-rich glycoproteins, and increases in hydrolytic enzymes such as chitinase and glucanase.

Phytoalexins are low molecular weight compounds which accumulate as a result of pathogen challenge, have antimicrobial activity, and have proved to be of critical importance in disease resistance in several plant:pathogen interactions (Darvill et al., 1984, Annu. Rev. Plant Physiol. 35:243; Dixon et al., 1990, Adv. Genet. 28:165–234; and Kuc and Rush, 1895, Arch. Biochem. Biophys. 236:455–472). Terpenoid phytoalexins represent one of the major classes of plant defense compounds and are present across a wide range of plant species including conifers, monocots and dicots. The regulation of terpenoid phytoalexin biosynthesis has been most extensively studied among the solanaceae (e.g., tomato, tobacco, potato), however, most important crop species utilize this pathway in disease resistance.

In well characterized plant:microbe interactions, resistance to pathogens depends on the rate at which defense responses are activated (Dixon and Harrison, 1990, Adv. Genet. 28:165–234). In an incompatible interaction, the pathogen triggers a very rapid response, termed hypersensitive resistance (HR), localized to the site of ingress. In the susceptible host, no induction of defense responses is seen until significant damage is done to host tissue.

Defense-responses, including phytoalexin accumulation, can also be induced in plant cell cultures by compounds, termed "elicitors", for example components derived from the cell walls of plant pathogens (Cramer et al., 1985, EMBO J. 4:285–289; Cramer et al., 1985, Science 227:1240–1243; Dron et al., 1988, Proc. Natl. Acad. Sci. USA 85:6738–6742). In tobacco cell cultures, fungal elicitors trigger a coordinate increase in sesquiterpene phytoalexin biosynthetic enzymes and a concomitant decrease in squalene synthetase which directs isoprene intermediates into sterol biosynthesis (Chappell and Nable, 1987, Plant Physiol. 85:469–473; Chappell et al., 1991, Plant Physiol. 97:693–698; Threlfall and Whitehead, 1988, Phytochem. 27:2567–2580).

2.2. PHYSIOLOGICAL ROLES OF HMGR IN PLANTS

A key enzyme involved in phytoalexin biosynthesis and, hence, plant defense against diseases and pests is 3-hydroxy-3-methylglutaryl CoA reductase (HMGR; EC 1.1.134). HMGR catalyzes the conversion of 3-hydroxy-3-methylglutaryl CoA to mevalonic acid. Mevalonic acid is an intermediate in the biosynthesis of a wide variety of isoprenoids including defense compounds such as phytoalexins.

In addition to phytoalexin biosynthesis, the mevalonate/isoprenoid pathway produces a diverse array of other biologically important compounds (see FIG. 1). They include growth regulators, pigments, defense compounds, UV-protectants, phytotoxins, and specialized terpenoids such as taxol, rubber, and compounds associated with insect attraction, fragrance, flavor, feeding deterrence and allelopathy. Many of these compounds have critical roles in cellular and biological functions such as membrane biogenesis, electron transport, protein prenylation, steroid hormone synthesis, intercellular signal transduction, photosynthesis, and reproduction.

The conversion of 3-hydroxy-3-methylglutaryl CoA to mevalonic acid appears to be the rate-limiting step of isoprenoid biosynthesis and, thus, the regulation of HMGR expression serves as a major control point for a diversity of plant processes including defense responses. Plant HMGR levels change in response to a variety of external stimuli including light, plant growth regulators, wounding, pathogen attack, exogenous sterols (Brooker and Russell, 1979, Arch. Biochem. Biophys. 198:323–334; Russell and Davidson, 1982, Biochem. Biophys. Res. Comm. 104:1537–1543; Wong et al., 1982, Arch. Biochem. Biophys. 216:631–638 and Yang et al., 1989, Mol. Plant-Microb. Interact. 2:195–201) and vary dramatically between tissues and developmental stages of plant growth (Bach et al., 1991, Lipids 26:637–648 and Narita and Gruissem, 1991, J. Cell. Biochem 15A:102(Abst)). Reflecting this complexity, multiple HMGR isozymes exist in plants which are differentially regulated and may be targeted to distinct organellar locations. In addition to microsomal locations, plant HMGR isozymes have been localized to mitochondrial and chloroplast membranes (Brooker and Russell, 1975, Arch. Biochem. Biophys. 167:730–737 and Wong et al., 1982, Arch. Biochem. Biophys. 216:631–638).

2.3. PLANT HMGR GENES

HMGR genomic or cDNA sequences have been reported for several plant species including tomato (Narita and Gruissem, 1989, Plant Cell 1:181–190; Park, 1990, *Lycopersicon esculentum* Mill. Ph.D. Dissertation, Virginia Polytechnic Institute and State University, Blacksburg, Va.), potato (Choi et al., 1992, Plant Cell 4:1333–1344 and Stermer et al., 1991, Physiol. Mol. Plant Pathol. 39:135–145), radish (Bach et al., 1991, American Oil Chemists Society, Champaign, Ill. page 29–49), *Arabidopsis thaliana* (Caelles et al., 1989, Plant Mol. Biol. 13:627–638; Learned and Fink, 1989, Proc. Natl. Acad. Sci. USA 86:2779–2783), *Nicotiana sylvestris* (Genschik et al., 1992, Plant Mol. Biol. 20:337–341), *Catharanthus roseus* (Maldonado-Mendoza et al., 1992, Plant Physiol. 100:1613–1614), the Hevea rubber tree (Chye et al., 1991, Plant Mol. Biol. 16:567–577) and wheat (Aoyagi et al., 1993, Plant Physiol. 102:622–638). Cloning of additional HMGR genes from rice (Nelson et al., 1991, Abstract 1322, 3rd Intl. Cong. Intl. Soc. Plant Mol. Biol., Tucson, Ariz.), and tomato (Narita et al., 1991, J. Cell. Biochem 15A:102 (Abst)) has also been reported but no DNA sequence information has been published for these HMGR genes. In all plants thus far investigated, HMGR is encoded by a small gene family of two (Arabidopsis) or more members (tomato, potato, Hevea). See Table 1 for a summary of published information pertaining to plant HMGR genes.

TABLE 1

SUMMARY OF CLONED PLANT HMGR SEQUENCES AND THEIR REGULATION.

| Species | HMGR gene | Description[a] | constit. | Regulation pollen | wound | pathogen[b] | other | Promoter[c] Analyses | Ref. |
|---|---|---|---|---|---|---|---|---|---|
| Lycopersicon esculentum (tomato) | hmg2 | G, cDNA, F, S | — | + | + | B, F, E, N | mature fruit | S, GUS, D | 1 |
| | hmg1 | cDNA, P, A | low | ? | ? | — | immat. fruit | — | 1, 2 |

TABLE 1-continued

SUMMARY OF CLONED PLANT HMGR SEQUENCES AND THEIR REGULATION.

| Species | HMGR gene | Description[a] | constit. | pollen | wound | pathogen[b] | other | Promoter[c] Analyses | Ref. |
|---|---|---|---|---|---|---|---|---|---|
| *Solanum* | hmg1 | cDNA, F, S | low | □ | + | — | elic. suppressed | GUS | 3, 4 |
| *tuberosum* | hmg2 | cNDA, P, S | — | ? | + | F, E | — | — | 3 |
| (potato) | hmg3 | cDNA, P, S | — | ? | + | F, E | — | — | 3 |
| *Nicotiana sylvestris* | hmgr | cDNA, F, S | + | ? |   | E, V | roots, protoplasts | — | 5 |
| *Arabidopsis* | hmg1 | cDNA, G, F, S | low | ? | ? | ? | — | — | 6 |
| *thaliana* | hmg2 | cDNA | — | ? | ? | ? | — | — | 7 |
| *Hevea* | hmg1 | G, cDNA, F, S | — | ? | ? | ? | laticifer, ethylene ind | — | 8 |
| *brasiliensis* | hmg2 | cDNA, P, S | ? | ? | ? | ? | — | — | 9 |
|   | hmg3 | cDNA, F, S | + |   |   |   | "housekeeping" | S | 8 |
| *Catharanthus roseus* | hmgr | cDNA, F, S | + | ? | ? | ? | — | — | 10 |
| *Raphanus sativus* | hmg1 | cDNA, F, S | ? | ? | ? | ? | — | — | 11 |
| (radish) | hmg2 | cDNA, F, S | ? | ? | ? | ? | etiolated seedlings | — |   |
| *Triticum* | hmgr10 | cDNA, P | low | ? | — | ? | callus | — | 12 |
| *aestivum* | hmgr18 | cDNA, P | + | ? | — | ? | callus | — |   |
| (wheat) | hmgr23 | cDNA, P | — | ? | — | ? | roots, callus | — |   |

Footnotes
[a]G, genomic clone; cDNA, complementary DNA generated from mRNA (lacks promoter, introns); F, full-length clone (contains entire coding sequence); P, partial sequence; GenEMBL accession numbers are listed
[b]Many of the HMGR sequences were not tested for induction by any of the following indicated inducing conditions and factors. These sequences are indicated as (?). Of the tested HMGR sequences, the indicated inducing conditions or factors are not meant to be exclusive, as a "tested" HMGR sequence may not have been tested with all of the following indicated inducing conditins and factors. For example, the potato hmg2 gene was not tested for induction by fungal pathogen infection or nematode infestation. INduced by bacterial pathogen (B), fungal pathogen (F), virus pathogen (V), parasitic nematode (N), or defense elicitors (E).
[c]Promoter has undergone sequence analysis (S), has been analyzed in transgenic plants by expression of promoter:reporter gene fusions (GUS), has undergone deletion analyses (D).
References and GenEMBL Accession Numbers[a]
1. This disclosure and [M63642]
2. Narita et al, 1989, Plant Cell 1:181–190.
3. Choi, et al., 1992, Plant Cell 4:1333–1344. [L01400; L01401; L01402]
4. Stermer et al., 1992, Phytopathology 82:1085 (Abstract).
5. Genschik et al., 1992. Plant Mol. Biol. 20:337–341. [X63649]
6. Learned and Fink, 1989, Proc. Natl. Acad. Sci. USA 86:2779–2783. [J04537]
7. Caelles et al., 1989, Plant Mol. Biol. 13:627–638. [X15032]
8. Chye et al., 1991, Plant Mol. Biol 16:567–577. [X54657; X54658; X54659]
9. Chye et al., 1992, Plant Mol. Biol 19:473–484.
10. Maldonado-Mendoza et al., 1992, Plant Physiol. 100:1613–1614. [M96068]
11. Bach et al., 1991, In Physiology and Biochemistry of Sterols (Patterson, G. and W. Nes, eds.), Am. Oil Chemists Soc., Champaign, IL, pp. 29–49.
12. Aoyagi et al., 1993, Plant Physiol. 102:623–628
[a]GenEMBL Accession Number are in brackets.

2.4. TOMATO HMGR GENES

Tomato HMGR genes have been isolated by direct probing of a tomato genomic library with yeast HMG1 cDNA sequences (Cramer et al., 1989, J. Cell. Biochem. 13D:M408; Park, 1990, *Lycopersicon esculentum* Mill. Ph.D. Dissertation, Virginia Polytechnic Institution and State University, Blacksburg, Va.). One of these genes, designated tomato HMG2, has been characterized further and the sequence of the coding region reported (Park et al., 1992, Plant Mol. Biol. 20:327–331; GenBank M63642). The nucleic acid sequence of tomato HMG2 has been compared to those of other plant HMGRs. Sequence comparisons within regions encoding the HMGR protein show identities in the range of 69 to 96%, with the most closely related sequences being a partial cDNA sequence of potato HMG2 (96% sequence identity for 744 bases at the C-terminus coding region) and an HMGR cDNA from Nicotiana sylvestris (89% sequence identity; entire coding region). The tomato HMG2 gene is distinct from tomato HMG1 showing 78% sequence identity within the region encoding the N-terminus (1067 bases compared; see FIGS. 2A–2E). Comparisons of sequences outside the coding region (e.g., the 5'-untranslated leader sequence) reveal very little sequence conservation between divergent species and only limited homology among HMGR genes within the Solanaceae. Tomato HMG2 shows less than 75% sequence identity over an 81 base stretch with the *N. Sylvestris* leader sequences. Comparisons between the 5'-leader sequences of tomato HMG1 and HMG2 are included in FIGS. 2A–2E.

The coding region of the tomato HMG2 gene is interrupted by three introns and encodes a protein with a calculated molecular mass of 64,714 (Park et al., 1992, Plant Mol. Biol. 20:327–331). Table 2 shows a comparison of the derived amino acid sequence of the tomato HMG2 to HMGRs of other organisms. The N-terminal membrane domain of the tomato HMGR2 (the protein encoded by the HMG2 gene) is significantly smaller, shows no sequence similarity to the yeast or animal transmembrane domain, and contains 1–2 potential membrane spanning regions compared to 7–8 postulated in non-plant HMGRs (Basson et al., 1988, Mol. Cell Biol. 8:3797–3808; Liscum et al., 1985, J. Biol. Chem 260:522–530). This transmembrane domain is also highly divergent among plant species and among HMGR isogenes within a species although the actual membrane spanning residues are quite conserved.

Amino acid sequence comparisons between the N terminal two hundred residues of tomato HMGR2 and other plant HMGRs yield sequence identities in the range of 44–85%

(Table 2). The amino acid sequences of tomato HMGR1 and HMGR2 show only 75% sequence identity in this region. The catalytic domain of tomato HMGR2, located within the C-terminal 400 amino acids, shows significant sequence homology with the yeast (56% identity; 75% similarity) and human (55% identity; 75% similarity) HMGRs. This domain is highly conserved between plant species: comparisons between tomato HMGR2 (residues 200–602) and other plant HMGRs yields amino acid identities ranging from 74–90% (see Table 2).

In contrast to the information available on plant HMGR coding sequences, relatively little is known of the structure of plant HMGR promoters. Indeed, to date only one plant HMGR promoter sequence has been reported (Chye et al., 1991, Plant Mol. Biol. 16:567–577).

63:826–829 and Stermer and Bostock, 1987, Plant Physiol. 84:404–408). In cultured cells, the induction occurs with the addition of elicitors isolated from the cell walls of pathogenic microbes (Chappell et al., 1991, Plant Physiol. 97:693–698 and Stermer and Bostock, 1987, Plant Physiol. 84:404–408). Typically, elicitor treatment results in a marked, transient increase in HMGR mRNA level that is typical of transcriptionally regulated defense genes in plants (Cramer et al., 1985, EMBO J. 4:285–289; Dixon and Harrison, 1990, Adv. Genet. 28:165–234; Yang et al., 1991, Plant Cell 3:397–405).

The rapid pathogen-induced HMGR expression appears to be encoded by the HMG2 HMGR isogene. This has been established in tomato cells treated with elicitors (Park, 1990, *Lycopersicon esculentum* Mill. Ph.D. Dissertation, Virginia

TABLE 2

Amino acid identity (%) of the membrane and catalytic domains of plant HMGRs.

| | Solanaceae | | | | Euphorb. | | Apo | Brassicaceae | | |
|---|---|---|---|---|---|---|---|---|---|---|
| | Tom1 | Tom2 | Pot1 | Pot3 | Nic | Hev1 | Hev3 | Car | Ara1 | Rad1 | Rad2 |
| Tom1 | 100 | 75 | 98 | — | 77 | 46 | 53 | 64 | 57 | 48 | 57 |
| | — | — | — | — | — | — | — | — | — | — | — |
| Tom2 | | 100 | 74 | — | 85 | 44 | 52 | 66 | 50 | 48 | 52 |
| | | 100 | 90 | 90 | 95 | 85 | 74 | 84 | 81 | 80 | 80 |
| Pot1 | | | 100 | — | 76 | 45 | 54 | 63 | 58 | 49 | 57 |
| | | | 100 | 90 | 93 | 88 | 85 | 88 | 83 | 83 | 83 |
| Pot3 | | | | — | — | — | — | — | — | — | — |
| | | | | 100 | 92 | 86 | 85 | 84 | 82 | 81 | 82 |
| Nic | | | | | 100 | 42 | 49 | 63 | 54 | 49 | 57 |
| | | | | | 100 | 87 | 86 | 87 | 83 | 83 | 82 |
| Hev1 | | | | | | 100 | 44 | 38 | 76 | 51 | 55 |
| | | | | | | 100 | 86 | 87 | 86 | 86 | 85 |
| Hev3 | | | | | | | 100 | 46 | 56 | 48 | 48 |
| | | | | | | | 100 | 85 | 82 | 82 | 82 |
| Car | | | | | | | | 100 | 48 | 44 | 49 |
| | | | | | | | | 100 | 81 | 82 | 82 |
| Ara1 | | | | | | | | | 100 | 73 | 78 |
| | | | | | | | | | 100 | 94 | 95 |
| Rad1 | | | | | | | | | | 100 | 72 |
| | | | | | | | | | | 100 | 93 |
| Rad2 | | | | | | | | | | | 100 |
| | | | | | | | | | | | 100 |

Upper row: membrane domains (1 to 200 amino acids); Lower row: catalytic domain (201 to 600 amino acids). Plant species and hmgr isogene (where designated) are indicated: *L. esculentum* [tomato hmg1 (incomplete sequence) and hmg2; Tom1, Tom2], *S. tuberosum* [potato; Pot1, Pot3 (incomplete seq.)], *N. sylvestris* (Nic, isogene unknown), *A. thaliana* hmg1 (Ara1), *H. brasiliensis* (rubber tree; Hev1, Hev3), *C. roseus* (Car, isogene unknown), and *R. sativus* (radish; Rad1, Rad2). Comparisons are based on the sequences available from GenBank.
Euphorb.: Euphoriaceae, Apo.: Apocynaceae.

2.5 THE FUNCTIONS AND EXPRESSION PATTERNS OF DIFFERENT HMGR GENES

Specific plant HMGR isogenes show very distinct patterns of regulation during development and in response to pathogen infection or pest infestation (Caelles et al., 1989, Plant Mol. Biol. 13:627–638; Choi et al., 1992, Plant Cell 4:1333–1344; Chye et al., 1992, Plant Mol. Biol. 19:473–484; Narita and Gruissem, 1989, Plant Cell 1:181–190; Park et al., 1992, Plant Mol. Biol. 20:327–331; Park, 1990, *Lycopersicon esculentum* Mill. Ph.D. Dissertation, Virginia Polytechnic Institute and State University, Blacksburg, Va.; Yang et al., 1991, Plant Cell 3:397–405).

In the Solanaceae, the pathogen-induced synthesis of phytoalexin antibiotics is due to the induction of microsome-associated HMGR (Shih and Kuc, 1973, Phytopathology 63:826–829 and Stermer and Bostock, 1987, Plant Physiol. 84:404–408). In cultured cells, the induction occurs with the addition of elicitors isolated from the cell walls of pathogenic microbes (Chappell et al., 1991, Plant Physiol. 97:693–698 and Stermer and Bostock, 1987, Plant Physiol. 84:404–408). Typically, elicitor treatment results in a marked, transient increase in HMGR mRNA level that is typical of transcriptionally regulated defense genes in plants (Cramer et al., 1985, EMBO J. 4:285–289; Dixon and Harrison, 1990, Adv. Genet. 28:165–234; Yang et al., 1991, Plant Cell 3:397–405).

Polytechnic Institute and State University, Blacksburg, Va.) and in potato tubers infected with the soft-rotting bacterium *Erwinia carotovora* (Yang et al., 1991, Plant Cell 3:397–405). In potato tuber, HMG2 mRNA levels increased 20-fold within 14 hr following bacteria inoculation but was not induced by wounding in the absence of pathogen (Yang et al., 1991, Plant Cell 3:397–405).

HMG2 expression has been shown to be critical to disease resistance. An elicitor, arachidonic acid, induces defense responses including increases in HMG2 mRNA and thus, phytoalexin synthesis in potato tubers (Stermer and Bostock, 1987, Plant Physiol. 84:404–408 and Yang et al., 1991, Plant Cell 3:397–405). Tubers treated with arachidonic acid 48 hr prior to inoculation with *Erwinia carotovora* were completely resistant to rotting. Tubers inhibited in HMGR activity by mevinolin (an HMGR-specific competitive inhibitor) showed significantly increased rotting (Yang et al., 1991, Plant Cell 3:397–405).

Homologs to the tomato HMG2 HMGR isogene, based on analogous expression patterns, exist in other plants. For example, potato HMG2 and HMG3 mRNAs are also induced in response to wounding, elicitors and bacterial pathogens (Choi et al., 1992, Plant Cell 4:1333–1344 and Yang et al., 1991, Plant Cell 3:397–405). 405). An HMGR isogene isolated from *Nicotiana sylvestris* is induced by virus inoculation and defense elicitors (Genschik et al., 1992, Plant Mol. Biol. 20:337–341). Similarly, a HMGR isogene of rice is also induced by wounding and elicitors (Nelson et al., 1991, Abst 1322, 3rd Intl. Cong. Intl. Soc. Plant Mol. Biol., Tucson, Ariz.) suggesting that defense-specific HMG2 homologs are also present in monocotyledonous plants. However, the three HMGR cDNAs isolated from wheat apparently are not wound-inducible (Aoyagi et al., 1993, Plant Physiol. 102:623–628). Although DNA sequences have not been isolated, increases in HMGR enzyme activity in response to bacterial or fungal pathogens have been documented in a number of other plant species suggesting that the HMG2 isogene is widely represented among plants.

Tomato HMG2 is quite distinct from the tomato HMG1 isogene at the nucleic acid level (FIGS. 2A–2E). The HMG1 HMGR isogene appears to be expressed under circumstances that are different from those that induce the expression of the HMG2 gene. Narita and Gruissem have shown that tomato HMG1 is expressed at low levels in all tomato tissues analyzed and is highly expressed in immature fruit during the period of rapid growth (Narita and Gruissem, 1989, Plant Cell 1:181–190; Narita et al., 1991, J. Cell. Biochem. 15A:102(Abst)). Thus, tomato HMG1 may function in sterol synthesis and membrane biogenesis. Choi et al. have shown that potato HMG1 expression is induced in potato tubers by wounding but is suppressed by defense-elicitors or bacterial pathogens (Plant Cell 4:1333–1344). These data suggest that the HMGR encoded by the HMG1 is associated with the biosynthetic branch responsible for sterol production. Based on similarities in sequence or expression patterns (e.g. constitutive low level expression, suppression by elicitors or microbes, high expression during rapid cell division), Hevea HMGR3, potato HMG1, Arabidopsis HMG1, and radish HMG2 probably belong to this HMG1 HMGR isogene class.

2.6. PLANT HMGR PROMOTERS

Little is known of the promoters of plant HMGR genes. To date, there has been no known publications of studies analyzing the structure of plant HMGR promoters (e.g. deletion analyses, DNaseI footprint analysis, DNA-protein binding/gel retardation analyses). One article (Chye et al., 1991, Plant Mol. Biol. 16:567–577) documents approximately 1.5 kb of the upstream sequence of the Hevea HMG1 gene. This sequence shows no significant homology to the analogous region of the tomato HMG2 promoter disclosed herein. Another report cursorily mentioned expression of potato HMGR13 (presumably a HMG1 homolog) promoter:β-glucuronidase (GUS) fusions in transgenic tobacco (Stermer et al., 1992, Phytopathology 82:1085), but revealed no details concerning the promoter used nor the construction of the fusion.

3. SUMMARY OF THE INVENTION

The present invention relates to the use of plant promoter sequences responsive to wounding, pathogen infection, pest infestation as well as to elicitors or chemical inducers. The invention generally relates to the use of promoter sequences of 3-hydroxymethyl-3-glutaryl coA reductase (HMGR) genes, and specifically to the tomato HMG2 (HMGR2) promoter element and its homologs from other plant species, to control the expression of protein and RNA products in plants and plant cells. The invention further relates to the use of sequences from the tomato HMG2 promoter element or its homologs to modify or construct plant active promoters, which in turn may be used to control the expression of proteins and RNAs in plants and plant cells.

The tomato HMG2 promoter element and its homologs have a variety of uses, including but not limited to expressing or overexpressing heterologous genes in a variety of plant cell expression systems, plant cultures, or stably transformed higher plant species. Expression of the heterologous gene product may be induced by elicitor or chemical induction in plant cell expression systems, or in response to wounding, pathogen infection, pest infestation as well as elicitor or chemical induction in plants.

The use of the promoter elements described herein to engineer plants may have particular value. By way of illustration, and not by limitation, an agronomically important plant may be stably transformed with a HMG2 or HMG2 homolog promoter element or a promoter derived therefrom controlling a gene which confers resistance to pathogen infection or pest infestation. When such a plant is invaded by a pathogen or pest, the invasion will trigger the expression of the HMG2 or HMG2-homolog promoter element-controlled resistance gene and cause the plant to become increasingly resistant to the pathogen or pest at the site of invasion.

Further, a plant or a plant cell line may be stably transformed with a HMG2 or HMG2-homolog promoter element or a promoter derived therefrom controlling a gene which encodes a useful product that is, however, adverse to plant growth or development. In such a plant or cell line, the expression of the plant-deleterious product would remain dormant during the growth of the plant or cell line, thus allowing for productive and efficient cultivation or culturing of the engineered plant or cell line. When the engineered plant or cell line has attained optimal condition for harvest, the expression of the desired gene may be artificially triggered by mechanical wounding and/or elicitor or chemical induction. The desired product, either encoded by the induced gene or a compound produced by the induced gene product, may then be extracted from the induced plant, harvested plant tissue, or cell line after allowing for a short expression period. This production method is possible with plant tissues because, unlike animals, they remain metabolically active long after harvest.

Similarly, a plant or a plant cell line may also be stably transformed with a HMG2 or HMG2-homolog promoter element or a promoter derived therefrom controlling a gene that encodes a labile gene product or a gene product that synthesizes a labile compound. In such a plant or cell line, the expression of the labile gene product or compound is deferred until the optimal condition is attained for harvesting or processing of the desired product or compound. The synthesis of the desired product may then be induced in the plant or cell line by mechanical wounding and/or elicitor or chemical induction and the product expeditiously extracted from the induced plant or cell line after allowing for a short expression period.

3.1. Definitions

The terms listed below, as used herein, will have the meaning indicated.

| | |
|---|---|
| 35S = | cauliflower mosaic virus promoter for the 35S transcript |
| CAT = | chloramphenicol acetyltransferase |
| cDNA = | complementary DNA |
| cis-regulatory element = | A promoter sequence 5' upstream of the TATA box that confers specific regulatory response to a promoter containing such an element. A promoter may contain one or more cis-regulatory elements, each responsible for a particular regulatory response. |
| DNA = | deoxyribonucleic acid |
| gene fusion = | a gene construct comprising a promoter operably linked to a heterologous gene, wherein said promoter controls the transciption of the heterologous gene |
| GUS = | 1,3-β-Glucuronidase |
| heterologous gene = | In the context of gene constructs, a heterologous gene means that the gene is linked to a promoter that said gene is not naturally linked to. The heterologous gene may or may not be from the organism contributing said promoter. The heterologous gene may encode messenger RNA (mRNA), antisense RNA or ribozymes. |
| HMGR = | 3-hydroxy-3-methylglutaryl CoA Reductase |
| HMG2 homolog = | A plant promoter sequence which selectively hybridizes to a known HMG2 promoter (e.g. the toomato HMG2 promoter element disclosed herein), or the promoter of a HMGR gene that displays the same regulatory responses as a HMG2 promoter (ie. promoter activity is induced by wounding, pathogen-infection, pest-infestation, or elicitor treatment). |
| mRNA = | messenger RNA |
| operably linked = | A linkage between a promoter and gene sequence such that the transciption of said gene sequence is controlled by said promoter. |
| RNA = | ribonucleic acid |
| RNase = | ribonuclease. |

4. DESCRIPTION OF THE FIGURES

FIG. 1. The mevalonate/isoprenoid pathway in plants. PGR, plant growth regulators.

FIGS. 2A–2E. Nucleic acid sequence comparison of tomato HMG2 (SEQ ID NO:1) and tomato HMG1 (SEQ ID NO:2). Sequences are aligned by the algorithm of Smith and Waterman (Devereux et al., 1984, Nucl. Acid Res. 12:387–395) which inserts gaps indicated by dots to optimize alignment. The transcriptional initiation sites are indicated by +1 and arrow. The translational start codons and TATAA boxes are underlined. The comparison ends at the first intron of each gene. Ambiguous bases are indicated by lower case letters.

Figure 3:
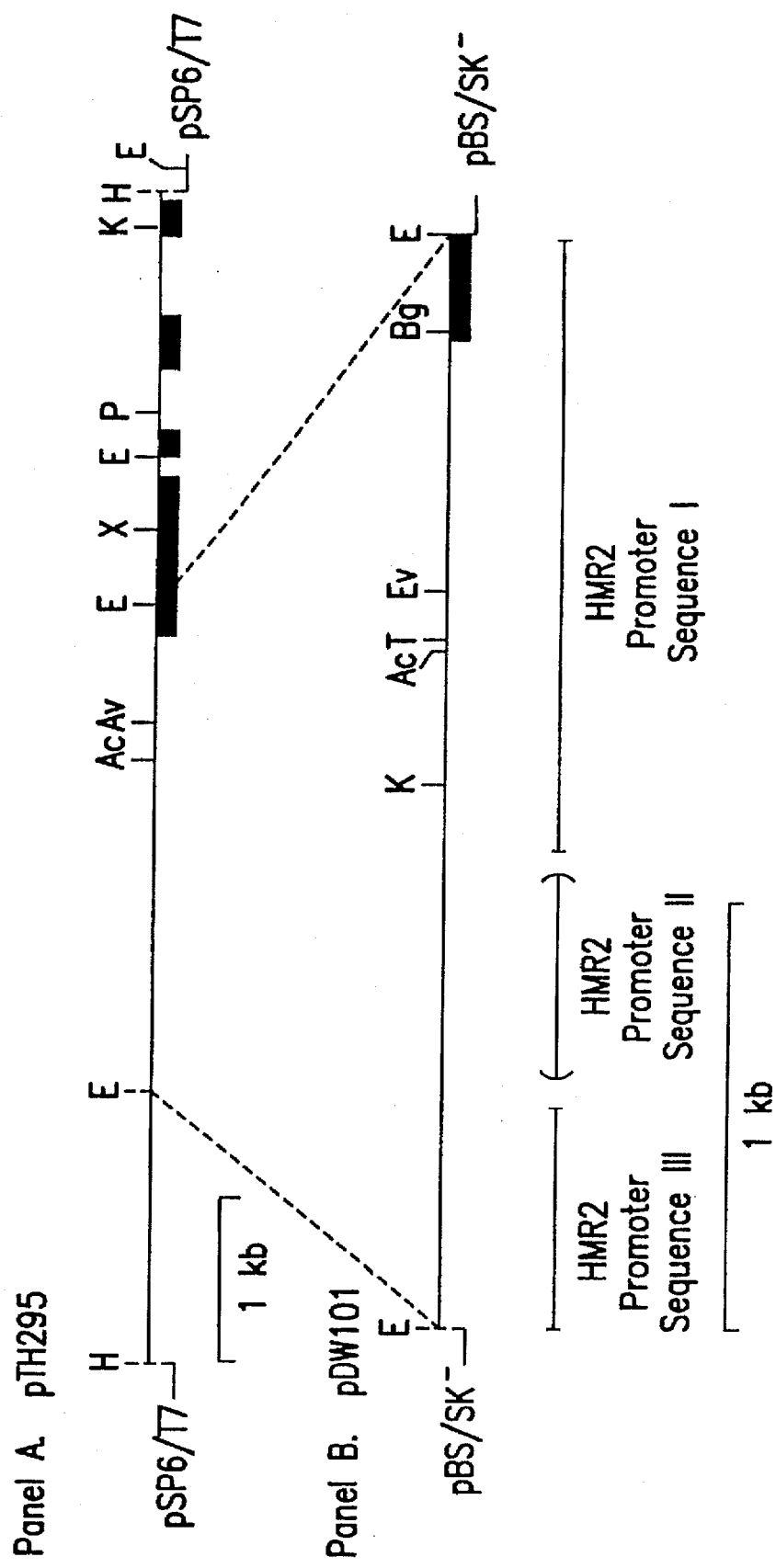

FIG. 3. Schematic of tomato HMG2 promoter. Panel A The tomato HMG2 genomic DNA insert of pTH295. Panel B The 2.5 kb EcoRI fragment of pTH295 used to general pDW101. pTH295 contains an approximately 7 kb HindIII fragment from the original lambda genomic clone inserted into the HindIII site of the multiple cloning region of bacterial plasmid pSP6/T7 (BRL). pDW101 contains a 2.5 kb EcoRI fragment of pTH295 inserted at the EcoRI site of plasmid bluescript SK-(Stratagene). Restriction endonucleases: Ac, AccI; Av, AvaI; Bg, BglII; E, EcoRI; Ev, EcoRV; H, HindIII; K, KpnI, P, PstI; T, TaqI; X, XbaI. The solid boxes represent the four exons encoding HMG2 protein. The fragments below pDW101 indicate the location of the HMG2 promoter sequences described in FIGS. 4A–4C, 5, and 6. The parentheses around HMG2 Sequence 2 indicate that the exact location within this region has not yet been determined.

FIGS. 4A–4C. Nucleic acid sequence of HMG2 Promoter Sequence I (SEQ ID NO:3). This 1388 bp sequence (SEQ ID NO:3) is from the 3'-end of the 2.5 kb EcoRI insert of pDW101. The transcriptional (+1) and translational (ATG) start sites are indicated. The TATAA box, PCR primer locations, and relevant restriction enzyme sites are underlined. Lower case letters indicate ambiguous bases.

FIG. 5. Nucleic acid sequence of HMG2 Promoter Sequence II (SEQ ID NO:4). The 480 bp sequence (SEQ ID NO:4) is from an internal region of the 2.5 kb EcoRI insert of pDW101. This region spans approximately −1,039 to −2,000 base pairs upstream of the HMG2 translation start site. The exact location of the sequence within this region remains to be determined. Two AT repeat motifs are underlined. An X indicates unknown bases; lower case letters are ambiguous bases.

FIG. 6. Nucleic acid sequence of HMG2 Promoter Sequence III (SEQ ID NO:5). The 415 bp sequence (SEQ ID NO:5) is from the 5'-end of the 2.5 kb EcoRI insert of pDW101. A 23 base palindromic sequence is underlined. Lower case letters are ambiguous bases.

Figure 7:
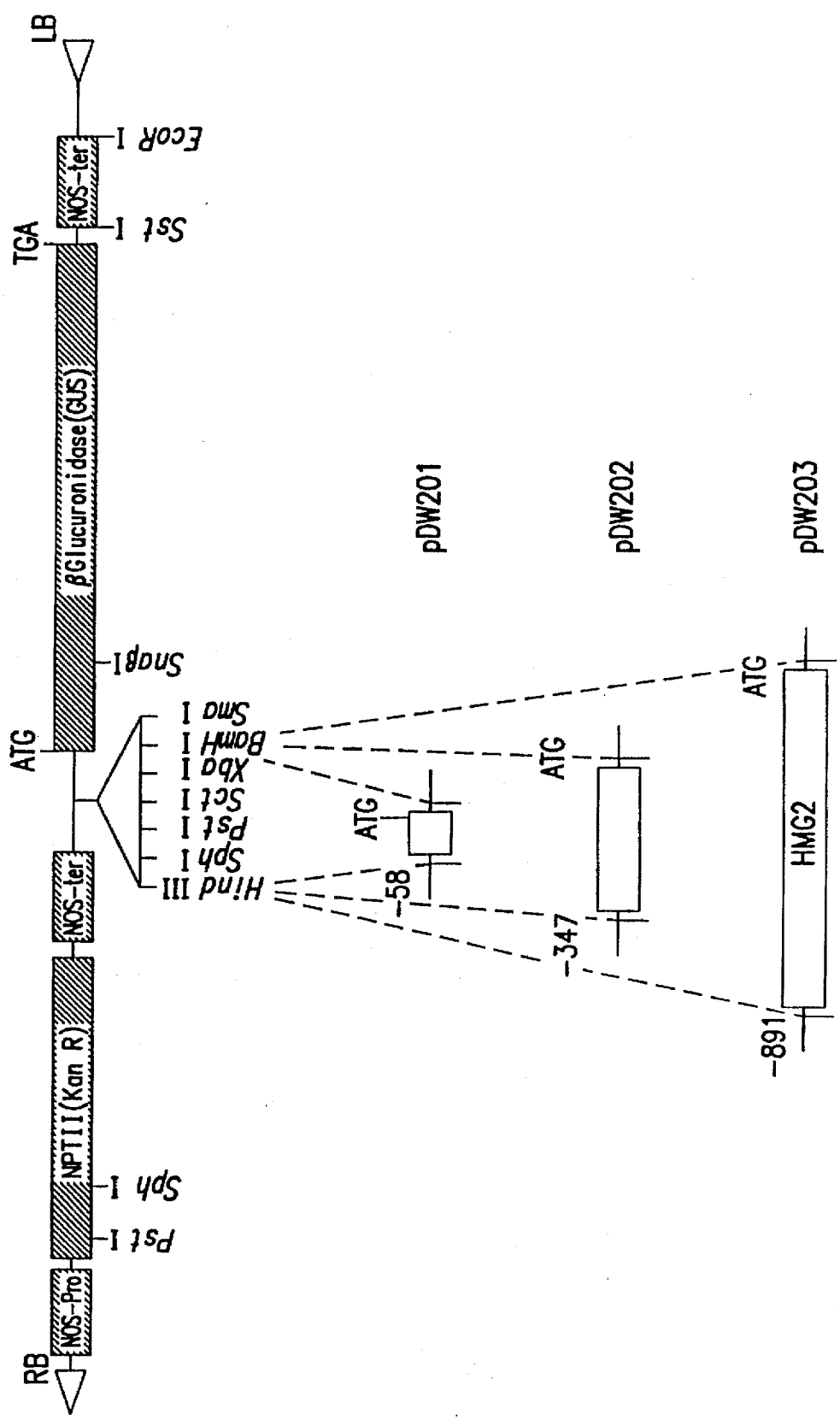

FIG. 7. Schematic representations of the promoter deletion clones, pDW201, pDW202 and pDW203, in pBI101. The open bars indicate the insert fragments from the tomato HMG2 promoter. RB and LB are T-DNA border sequences. The 5' HindIII and 3' BamHI sites flanking each HMG2 promoter region were generated within the sequence of the primers used to PCR-amplify these inserts.

Figure 8:
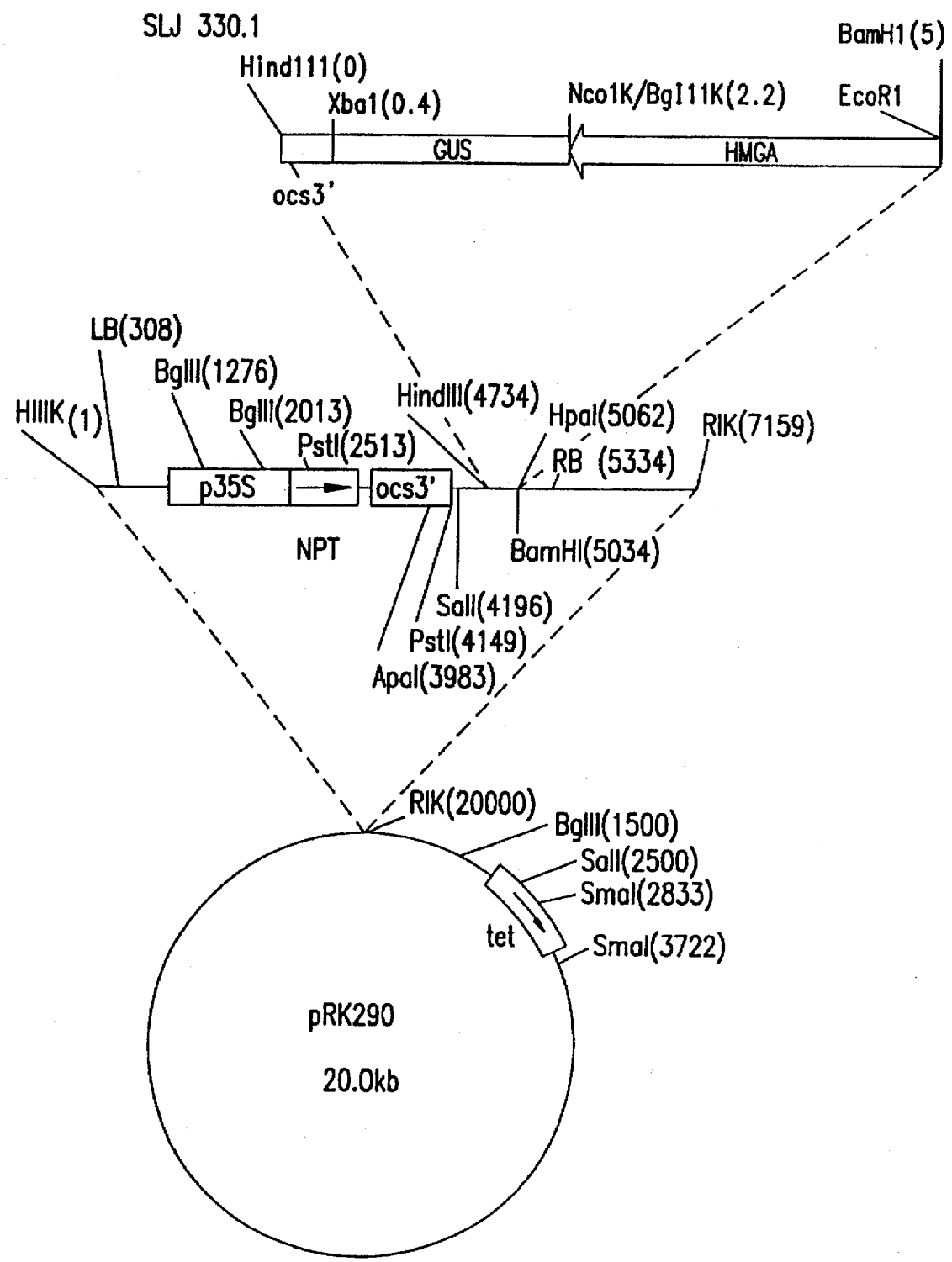

FIG. 8. Restriction map of plasmid pSLJ330.1. HMGA, EcoRI/BglII HMG2 promoter fragment from pDW101; GUS, beta glucuronidase coding sequence; ocs 3', 3' region and polyadenylation site derived from A. tumefaciens octopine synthetase gene; p35S, promoter of the cauliflower mosaic virus 35S transcript; NPT, NPTII gene encoding neomycin phosphotransferase conferring kanamycin resistance; LB,RB, left and right border sequences of Ti plasmids required for transfer of DNA from Agrobacterium to plant cell.

Figure 9:
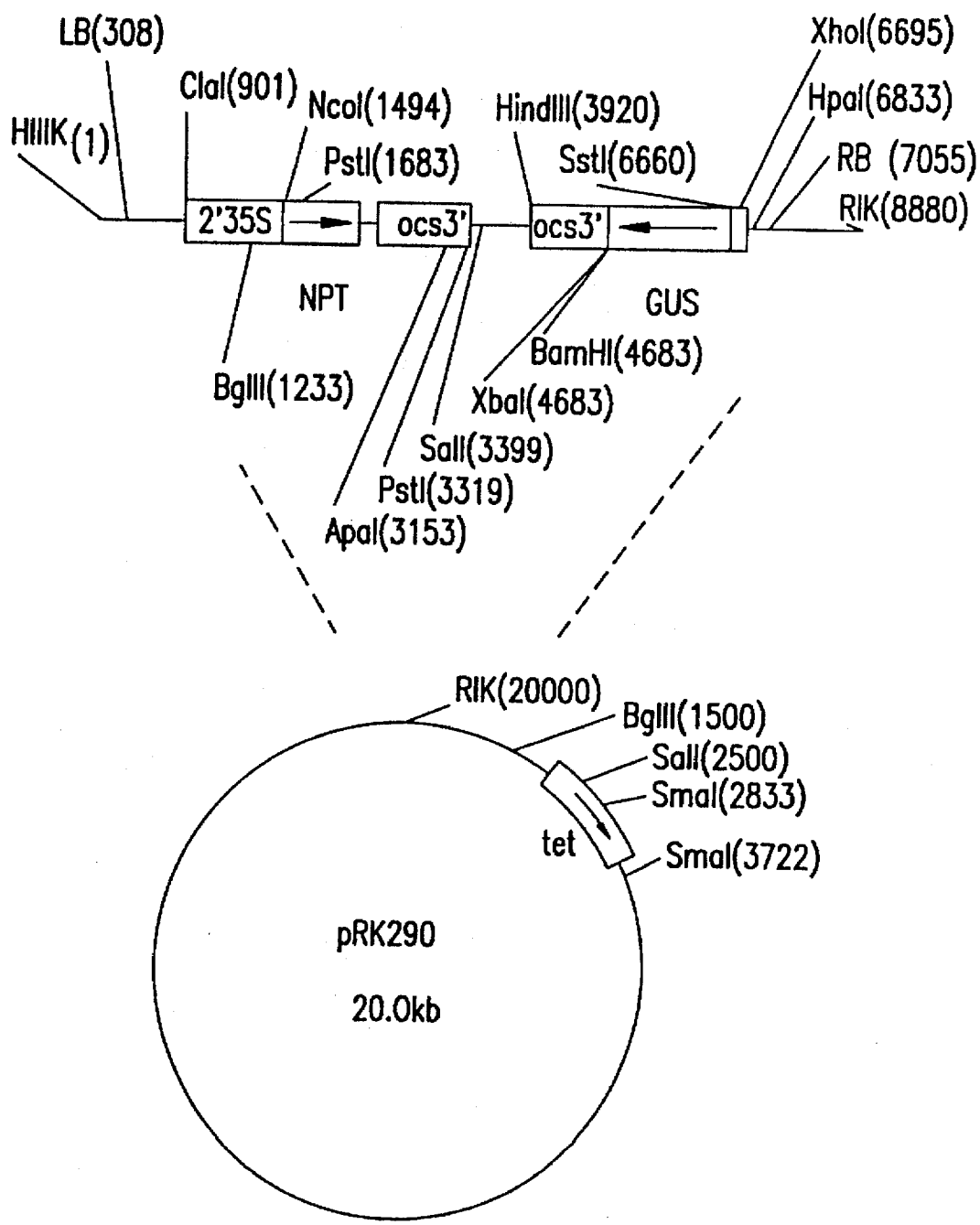

FIG. 9. Restriction map of plasmid pSLJ1911. This plasmid was used to transform plants with a 35S:GUS construct whose activity served as a benchmark to the various HMG2:GUS constructs. Abbreviations are as described in FIG. 8.

Figure 10A:
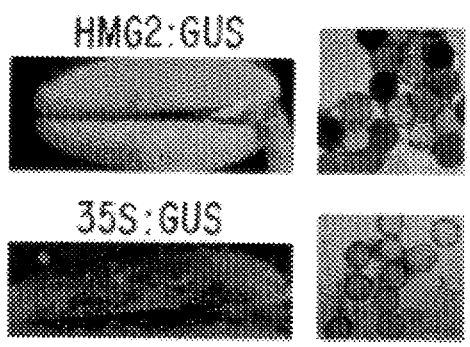
Figure 10B:
Figure 10C:
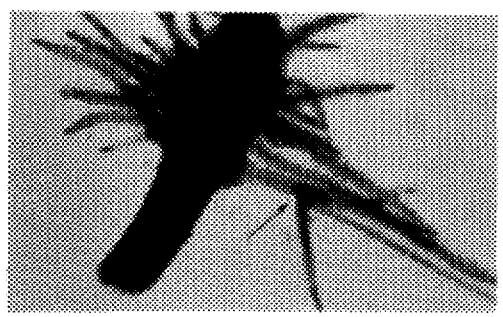

FIGS. 10A–10C. Tissue specificity of HMG2 Promoter expression in transgenic tobacco and tomato plants. Blue color indicates regions where GUS is active. FIG. 10A. Anthers and pollen of HMG2:GUS compared to analogous tissues from 35S:GUS constructs (plants transformed with pSLJ330.1 or pSLJ1911, respectively). FIG. 10B. Trichomes of fully-expanded tobacco leaf (transformation vector pSLJ330.1). FIG. 10C. Root section of tomato seedling transformed with pSLJ330.1. Seedling was grown axenically on agar medium. Arrow indicates the location of lateral root initiation.

Figure 11A:
Figure 11B:
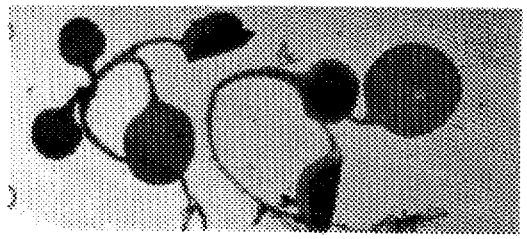
Figure 11C:
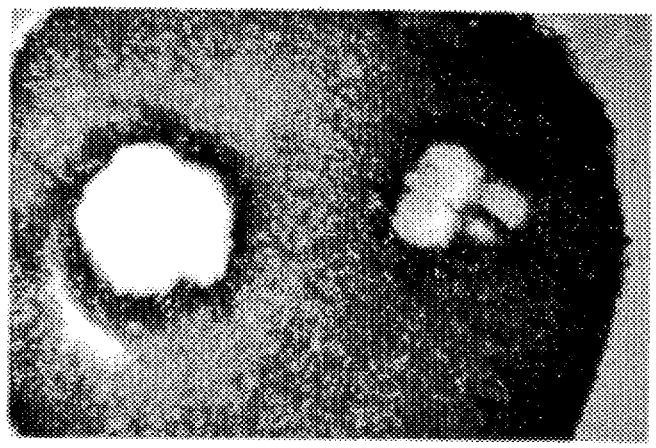

FIGS. 11A–11C. Defense-related HMG2 Promoter expression in tobacco transformed with pSJL330.1.

FIG. 11A. Leaf tissue 24 (2 left wells) and 48 hours after wounding and inoculating with water (W, mock) or soft-rotting bacterium *Erwinia carotovora* ssp. carotovora strain EC14 (EC).

FIG. 11B. Tobacco seedlings (14 days post germination in sterile potting mix) 24 and 48 hours following inoculation at site indicated by arrow by placing Rhizoctonia infected oat seed in direct contact with stem.

FIG. 11C. Leaf section of field grown tobacco showing GUS activity surrounding necrotic regions due to natural insect predation. Blue pigmentation at the outside edge of disk is due to wound response.

FIGS. 12A–12E. Nematode response of HMG2:GUS transgenic tomato (transformed with pSLJ330.1). Tomato seedlings were inoculated with *Meloidogyne hapla* second stage juveniles. At the indicated times after inoculation, roots were harvested, incubated overnight in X-Gluc to stain for GUS activity, and subsequently counter-stained with acid fucsin to visualize nematodes.

Figure 12A:
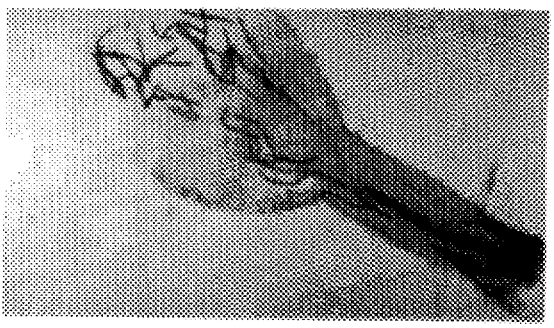

FIG. 12A. Squash of root tip 2 days after inoculation.

Figure 12D:
Figure 12B:

FIG. 12B. Root region 3 days post-inoculation. Arrow indicates region showing initial GUS activity.

Figure 12C:
Figure 12E:
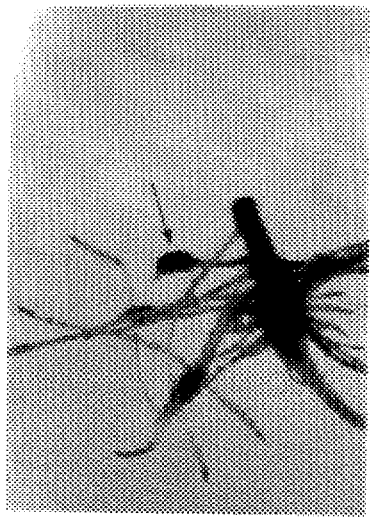

FIG. 12C–12E. Root tips showing characteristic nematode-induced swelling 7 days post-inoculation. Note in Panel E that uninfected root tips show no GUS activity.

5. DESCRIPTION OF THE INVENTION

The present invention relates to the HMG2 promoter and its homologs that are involved in the plant response to pathogen infections, pest infestations or mechanical wounding, and their use to drive the expression of heterologous genes.

The tomato HMG2 promoter and its homologs control the expression of a 3-hydroxy-3-methylglutaryl CoA reductase (HMGR) isozyme in plants. HMGR catalyzes the production of mevalonic acid, which is an intermediate in the biosyntheses of various secondary metabolites that have critical roles in plant defense responses and plant development. In most plant tissues, tomato HMG2 promoter and its homologs remain dormant until their activity is triggered by pathogen infections, pest infestations or mechanical wounding. The induction of the HMG2 and homologous promoters are mediated in part by so called "elicitor" compounds derived from constituents of plant (Darvill and Albersheim, 1984, Annu. Rev. Plant Physiol. 35:234) or plant pathogen cell wall or surface components. When induced, the HMG2 promoter and its homologs effect rapid and strong expression of the genes under their control. The lack of significant constitutive expression and the rapidly inducible, strong expression characteristics of the HMG2 and homologous promoters make them ideal elements for controlling the expression of various types of heterologous genes. Such genes include those encoding pathogen and pest resistance functions, products that are directly or indirectly deleterious to plant growth, labile products, or products involved in the biosyntheses of labile compounds, to name but a few.

According to the invention, heterologous genes can be placed under the control of the tomato HMG2 or homologous promoter elements or promoters derived therefrom, all described herein, and used to engineer cell culture expression systems, or transgenic plants. Expression of the heterologous gene will be induced in response to pathogen infection, pest infestation, mechanical wounding or chemical or elicitor treatment. For example, the induction of the heterologous gene in plant cell culture or plant may be induced by treatments with cell wall extracts of plant pathogens, purified elicitors contained within such extracts, or synthetic functional analogs of those elicitors. Alternatively, the expression of the heterologous gene in the plant may be induced by various bacterial or fungal plant pathogen infections. Similarly, the induction may also be triggered by infestation of the plant by pests such as insects and nematodes.

The invention relates to the family of HMG2 and HMG2-derived promoters, and for the purpose of description only, the invention will be divided into several stages: (a) isolation, identification and characterization of HMG2 promoter sequences; (b) identification and characterization of cis-regulatory elements within the HMG2 promoter that can regulate other plant promoter sequences; (c) construction of chimeric genes with a heterologous gene of interest operably associated with different portions of the HMG2 promoter element or with a plant-active promoter modified with HMG2 cis-regulatory elements; (d) engineering the gene of interest controlled by a HMG2 promoter element or HMG2-derived promoter into a transgenic plant or plant cell; (e) inducing the expression of said constructs and the production of the gene product of interest in plant tissues or cell culture systems; and (f) the types of heterologous gene products that would be advantageously produced under the control of HMG2 promoter elements and HMG2-derived promoters According to the present invention, functional portions of HMG2 promoters described herein refer to regions of the nucleic acid sequence which are capable of promoting transcription of an operably linked gene in response to wounding, pathogen infection, pest infestation or chemical/elicitor treatment during the entire pattern of plant development. Nucleotide sequences homologous to the tomato HMG2 promoter described herein refers to nucleic acid sequences which are capable of selectively hybridizing to the nucleic acid sequence contained in the approximately 2.2 kb EcoRI-BqlII fragment of pDW101 in hybridization assays or which are homologous by sequence analysis (containing a span of 10 or more nucleotides in which at least 50 percent of the nucleotides are identical to the sequences presented herein). Homologous nucleotide sequences refer to nucleotide sequences including, but not limited to, HMG2 promoter elements in diverse plant species as well as genetically engineered derivatives of the promoter elements described herein. The various embodiments of the claimed invention presented herein are by the way of illustration and are not meant to limit the invention.

5.1 HMG2 Promoters

Methods which could be used for the synthesis, isolation, molecular cloning, characterization and manipulation of the HMG2 promoter sequences described herein are well known to those skilled in the art. See, e.g., the techniques described in Sambrook et al., Molecular Cloning: A Laboratory Manual, 2nd. ed., Cold Spring Harbor Laboratory, Cold Spring Harbor, N.Y. (1989).

According to the present invention, the HMG2 promoter sequences or portions thereof described herein may be obtained from an appropriate plant source, from cell lines or recombinant DNA constructs containing the HMG2 promoter sequences, and/or by chemical synthetic methods. For example, chemical synthetic methods which are well known to those skilled in the art can be used to synthesize sequences depicted in FIGS. 4A–4C, 5 and 6 herein (SEQ ID NO:3, SEQ ID NO:4, SEQ ID NO:5, respectively). These sequences can be cloned and expanded for use as HMG2 promoter elements. Such synthetic sequences can also be used as hybridization probes to identify and isolate HMG2 promoter sequences from appropriate plant and cellular sources.

Alternatively, a HMG2 promoter element may be identified and isolated by screening gene libraries. For example, a genomic DNA library may be screened for clones containing sequences homologous to known HMGR genes or, alternatively, HMGR promoter sequences. For example, sequences from genomic or cDNA clones encoding HMGR or oligonucleotide probes corresponding to known HMGR amino acid sequences may be used as hybridization probes to identify homologous clones in a genomic DNA library using standard methods. Such methods include, for example, the method set forth in Benton and Davis (Science 196:180 (1977)) for bacteriophage libraries, and Grunstein and Hogness (Proc. Nat. Acad. Sci. U.S.A. 72:3961–3965 (1975)) for plasmid libraries.

In instances, where the species sources of the probe and the library are widely divergent, such as between a monocot and a dicot, the probe is preferably from a region encoding highly conserved amino acid residues of the HMGR and the hybridization and wash are carried out at low stringencies (see Park et al., 1992, Plant Mol. Biol. 20:327–331). Clones containing HMG2 sequences may be distinguished from other HMGR isogenes by their ability to detect at high stringency hybridization conditions mRNA transcripts that are rapidly induced by wounding, pathogen infection, pest-infestation, or elicitor treatment (for an example of such an analysis see Yang et al., 1991, Plant Cell 3:397–405). Alternatively, HMG2 clones may be identified by examining their ability to hybridize at moderate or high stringency conditions to 5' untranslated region or 5' upstream region of known HMG1 and HMG2 (e.g. the 2.5 kb EcoRI fragment depicted in FIG. 3) genes. HMG2 clones can be identified as those that show a stronger signal with the HMG2 probe than with the HMG1 probe.

In other instances, where the species sources of the probe and the library are not widely divergent, such as between closely related plants, the probes used to screen such libraries may consist of restriction fragments or nucleotide sequences encoding the N-terminal 200 amino acids of the tomato HMG2 HMGR (see Park et al., 1992, Plant Mol. Biol. 20:327–331), portions thereof or nucleotide sequences homologous thereto. Retrieved clones may then be analyzed by restriction fragment mapping and sequencing techniques according to methods well known in the art.

In another approach, restriction fragments or nucleotide sequences of the tomato HMG2 promoter elements described herein (FIG. 3, FIGS. 4A–4C, FIG. 5, and FIG. 6), portions thereof and sequences homologous thereto may be used to screen genomic libraries to identify genomic clones containing homologous promoter sequences using the standard techniques described supra. For example, the 2.5 kb EcoRI fragment containing the tomato HMG2 promoter in plasmid pDW101 or portions thereof may be used to such ends.

In the above two approaches, the hybridization and wash conditions used to identify clones containing tomato HMG2 homologous promoter sequences may be varied depending on the evolutionary relatedness between the species origins of the probe and the genomic library screened. The more distantly related organisms would require low stringency hybridization and wash conditions.

In yet another approach to the isolation of HMG2 promoter elements, oligonucleotide sequences from the tomato HMG2 promoter described herein could be used as primers in PCR (polymerase chain reactions) to generate HMG2 promoter sequences from any plant species. Similar to the hybridization approaches, the amplification protocol may be adjusted according to the evolutionary relatedness between the target organism and primer-source organism. The adjustments may include the use of degenerate primers and protocols well known in the art for amplifying homologous sequences. For a review of PCR techniques, see for example, Gelfind, 1989, *PCR Technology. Principles and Applications for DNA Amplification*, Ed., H. A. Erlich, Stockton Press, N.Y., and *Current Protocol in Molecular Biology*, Vol. 2, Ch. 15, Eds. Ausubel et al., John Wiley & Sons, 1988.

In instances where only internal sequences of a HMG2 promoter are known, sequences flanking such sequences may be obtained by inverse PCR amplification (Triglia et al., 1988, Nucl. Acids Res. 16:8186). The flanking sequences can then be linked to the internal HMG2 promoter sequences using standard recombinant DNA methods in order to reconstruct a sequence encompassing the entirety of the HMG2 promoter.

The location of the HMG2 promoter within the sequences isolated as described above may be identified using any method known in the art. For example, the 3'-end of the promoter may be identified by locating the transcription initiation site, which may be determined by methods such as RNase protection (Liang et al., 1989, J. Biol. Chem. 264:14486–14498), primer extension (Weissenborn and Larson, 1992, J. Biol. Chem. 267:6122–6131), or reverse transcriptase/PCR. The location of the 3'-end of the promoter may be confirmed by sequencing and computer analysis, examining for the canonical AGGA or CAT and TATA boxes of promoters that are typically 50–60 base pairs (bp) and 25–35 bp 5'-upstream of the transcription initiation site. The 5'-end of the promoter may be defined by deleting sequences from the 5'-end of the promoter-containing fragment, constructing a transcriptional or translational fusion of the resected fragment and a reporter gene, and examining the expression characteristics the chimeric gene in transgenic plants. Reporter genes that may be used to such ends include, but are not limited to, GUS, CAT, luciferase, β-galactosidase and C1 and R gene controlling anthocyanin production.

According to the present invention, a HMG2 promoter element is one that confers to an operably linked gene in a plant or plant cell: 1) minimal expression in most plant tissues; and 2) induced expression following wounding, pathogen infection, pest infestation or chemical/elicitor treatment. A HMG2 promoter element may additionally confer specific developmental expression as in pollen, mature fruit tissues, and root tissues of the zone of lateral root initiation. See Table 1, which compares the expression characteristics of tomato HMG2 promoter to the other known plant HMGR promoters.

According to the present invention, an embodiment of the HMG2 promoter element comprises the region between positions −2,300 and +1 in the 5' upstream region of the tomato HMG2 gene (see FIG. 3). Another embodiment of the HMG2 promoter element comprises the region between positions −891 and +1 in the 5' upstream region of the tomato HMG2 gene. An additional embodiment of HMG2 promoter element comprises the region between positions −347 and +1 in the 5' upstream region of the tomato HMG2 gene. Yet another embodiment of HMG2 promoter element comprises the region between positions −58 and +1 in the 5' upstream region of the tomato HMG2 gene. In further embodiments of the present invention, a HMG2 promoter element may comprise sequences that commence at position +1 and continue 5' upstream up to and including the whole of the nucleotide sequence depicted in FIGS. 4A–4C, FIG. 5 or FIG. 6.

5.2 Cis-Regulatory Elements of HMG2 Promoters

According to the present invention, the cis-regulatory elements within a HMG2 promoter may be identified using any method known in the art. For example, the location of cis-regulatory elements within a HMG2 promoter may be identified using methods such as DNase or chemical footprinting (Meier et al., 1991, Plant Cell 3:309–315) or gel retardation (Weissenborn and Larson, 1992, J. Biol. Chem. 267-6122–6131; Beato, 1989, Cell 56:335–344; Johnson et al., 1989, Ann. Rev. Biochem. 58:799–839). Additionally, resectioning experiments may also be employed to define the location of the cis-regulatory elements. For example, a HMG2 promoter-containing fragment may be resected from either the 5' or 3' end using restriction enzyme or exonuclease digests.

To determine the location of cis-regulatory elements within the sequence containing the HMG2 promoter, the 5'- or 3'-resected fragments, internal fragments to the HMG2 promoter containing sequence, or HMG2 promoter fragments containing sequences identified by footprinting or gel retardation experiments may be fused to the 5'-end of a truncated plant promoter, and the activity of the chimeric promoter in transgenic plant examined as described in section 5.1 above. Useful truncated promoters to these ends comprise sequences starting at or about the transcription initiation site and extending to no more than 150 bp 5' upstream. These truncated promoters generally are inactive or are only minimally active. Examples of such truncated plant promoters may include, among others, a "minimal" CaMV 35S promoter whose 5' end terminates at position −46 bp with respect to the transcription initiation site (Skriver et al., Proc. Nat. Acad. Sci. USA 88:7266–7270); the truncated "−90 35S" promoter in the X-GUS-90 vector (Benfy and Chua, 1989, Science 244:174–181); a truncated "−101 nos" promoter derived from the nopaline synthase promoter (Aryan et al., 1991, Mol. Gen. Genet. 225:65–71); and the truncated maize Adh-1 promoter in pADcat 2 (Ellis et al., 1987, EMBO J. 6:11–16).

According to the present invention, a HMG2 cis-regulatory element is a HMG2 promoter sequence that can confer to a truncated promoter one or more of the following characteristics in expressing an operably linked gene in a plant or plant cell: 1) induced expression following wounding; 2) induced expression following pathogen infection; 3) induced expression following pest infestation; 4) induced expression following chemical elicitor treatment; or 5) expression in pollen, mature fruit, or other developmentally defined tissues identified as expressing HMG2. Further, a HMG2 cis-regulatory element may confer, in addition to the above described characteristics, the ability to suppress the constitutive activity of a plant promoter.

5.3 HMG2 Promoter-Driven Gene Constructs

The properties of the nucleic acid sequences are varied as are the genetic structures of various potential host plant cells. The preferred embodiments of the present invention will describe a number of features which an artisan may recognize as not being absolutely essential, but clearly advantageous. These include methods of isolation, synthesis or construction of gene constructs, the manipulations of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present inventions, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The present invention provides for use of recombinant DNA constructs which contain the tomato HMG2 promoter fragments or sequences as depicted in FIGS. 3, 4A–4C (SEQ ID NO:3), 5 (SEQ ID NO:4), and 6 (SEQ ID NO5), functional portions thereof, and nucleotide sequences homologous thereto. The HMG2 promoter elements of the invention may be used to direct the expression of any desired protein, or to direct the expression of an RNA product, including, but not limited to, an "antisense" RNA or ribozyme. Such recombinant constructs generally comprise a HMG2 or HMG2-derived promoter as described herein, ligated to the nucleic acid sequence encoding a desired heterologous gene.

A HMG2-derived promoter is used herein to refer to a promoter that comprises a functional portion of a HMG2 promoter or a functional promoter that contains HMG2 promoter sequences and whose activity is regulated by the HMG2 promoter sequences. For example, a HMG2-derived promoter may comprise the approximately 0.17 kb, 0.46 kb or 1.0 kb HindIII-BamHI tomato HMG2 promoter fragment of pDW201, pDW202 and pDW203, respectively (see FIG. 7). Alternatively, a HMG2-derived promoter may be a chimeric promoter, comprising a full-length or truncated plant promoter modified by the attachment of one or more HMG2 cis-regulatory elements. The manner of chimeric promoter constructions may be any well known in the art. For examples of approaches that can be used in such constructions, see section 5.2 above and Fluhr et al., 1986, Science 232:1106–1112; Ellis et al., 1987, EMBO J. 6:11–16; Strittmatter and Chua, 1987, Proc. Nat. Acad. Sci. USA 84:8986–8990; Poulsen and Chua, 1988, Mol. Gen. Genet. 214:16–23; Comai et al., 1991, Plant Molec. Biol. 15:373–381; Aryan et al., 1991, Mol. Gen. Genet. 225:65–71.

According to the present invention, where a HMG2 or HMG2-derived promoter is used to express a desired protein, the DNA construct is designed so that the protein coding sequence is ligated in phase with the translational initiation codon downstream of the promoter. Where the promoter fragment is missing 5'-leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria, or vacuole).

5.4 Recombiant DNA Constructs

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible, selectable, or screenable marker genes for isolating, identifying or tracking plant cells transformed by these constructs. Selectable markers include, but are not limited to, genes that confer antibiotic resistance, (e.g., resistance to kanamycin or hygromycin) or herbicide resistance (e.g., resistance to sulfonylurea, phosphinothricin, or glyphosate). Screenable markers include, but are not be limited to, genes encoding β-glucuronidase (Jefferson, 1987, Plant Molec Biol. Rep 5:387–405), luciferase (Ow et al., 1986, Science 234:856–859), or B protein that regulate anthocyanin pigment production (Goff et al., 1990, EMBO J 9:2517–2522).

In embodiments of the present invention which utilize the *Agrobacterium tumefacien* system for transforming plants (see infra), the recombinant constructs may additionally comprise at least the right T-DNA border sequences flanking the DNA sequences to be transformed into the plant cell. Alternatively, the recombinant constructs may comprise the right and left T-DNA border sequences flanking the DNA sequence. The proper design and construction of such T-DNA based transformation vectors are well known to those skilled in the art.

5.5 Production of Transgenic Plants and Plant Cells

According to the present invention, a desirable plant or plant cell may be obtained by transforming a plant cell with the nucleic acid constructs described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium is employed to introduce the gene constructs into plants. Such transformations preferably use binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform as well as transfer DNA to monocotyledonous plants and plant cells. (see Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

According to the present invention, a wide variety of plants and plant cell systems may be engineered for the desired physiological and agronomic characteristics described herein using the nucleic acid constructs of the instant invention and the various transformation methods mentioned above. In preferred embodiments, target plants and plant cells for engineering include, but are not limited to, those of maize, wheat, rice, soybean, tomato, tobacco, carrots, peanut, potato, sugar beets, sunflower, yam, Arabidopsis, rape seed, and petunia.

5.6 Selection and Identification of Transformed Plants and Plant Cells

According to the present invention, desired plants and plant cells may be obtained by engineering the gene constructs described herein into a variety of plant cell types, including but not limited to, protoplasts, tissue culture cells, tissue and organ explants, pollen, and embryos as well as whole plants. In an embodiment of the present invention, the engineered plant material is selected or screened for transformants (i.e. those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g. the β-glucuronidase, luciferase, B or C1 genes) that may be present on the recombinant nucleic acid constructs of the present invention. Such selection and screening methodologies are well known to those skilled in the art.

Physical and biochemical methods also may be used to identify a plant or plant cell transformant containing the gene constructs of the present invention. These methods include but are not limited to: 1) Southern analysis or PCR amplification for detecting and determining the structure of the recombinant DNA insert; 2) northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, also may be used to detect the presence or expression of the recombinant construct in specific plant organs and tissues. The methods for doing all these assays are well known to those skilled in the art.

5.7. Expression of Heterologous Gene Products in Transgenic Plants

The present invention may be advantageously used to direct the expression of a variety of gene products. These gene products include, but are not limited to, proteins, anti-sense RNA and ribozymes.

In an embodiment of the present invention, a HMG2 or HMG2-derived promoter element which confers wound-inducible and/or elicitor-inducible gene expression may be used to express in plants and plant cell cultures a variety of high valued protein products, including, but not limited to, pharmaceuticals and therapeutic enzymes and proteins. Such protein products may include, for example, various peptide-hormones, cytokines, growth factors, antibodies, blood proteins and vaccines. Further, these promoter elements may also be used to express in plants and cell cultures multiple enzymes of complex biosynthetic pathways, the induction of which would confer to host plant or plant cell the ability to produce complex biochemicals and biologicals. Examples of such products include secondary metabolites such as alkaloids, antibiotics, pigments, steroids and complex biological structures such as intact or defective viruses or viral particles. Additionally, these promoter elements may also be used to express various types of lytic and processing enzymes that can convert what would be otherwise unusable or low quality plant compounds or constituents into useful or high quality compounds or chemical feedstocks. Examples of such products include cellulases, lignases, amylases, proteases, pectinases, phytases, etc. Furthermore, wound-inducible and/or elicitor-inducible HMG2 or HMG2-derived promoter elements may also be used to express RNA products such as antisense RNA and ribozymes.

In the above mentioned embodiment, the wound- and/or elicitor-specific HMG2 and HMG2-derived promoters may be advantageously used to direct the "post-harvest" production and accumulation of the desired direct or indirect gene products. That is, the production of the desired products does not occur during normal growth of the plant or the cell culture, but only occurs after the plant or the cell culture (e.g. callus culture) is mechanically macerated and/or elicitor treated shortly before, during or shortly after harvesting the plant or cell cultures. (For a general reference describing plant cell culture techniques that could be used in conjunction with the "post-harvest" production approach disclosed here, see Handbook of Plant Cell Culture, Vol. 4, Techniques and Applications, etc., Evans, D. A., Sharp, W. R. and Ammirato, P. V., 1986 Macmillan Publ., New York, N.Y.).

The application of the wound- and/or elicitor-induced specificity of HMG2 or HMG2-derived promoters to produce the above mentioned types of products is particularly significant given that many such products may be either labile or deleterious to cellular metabolism or plant growth. Thus, their efficient and optimal production, in many instances, may be best achieved by the use of wound-inducible or elicitor-inducible promoters coupled with a post-harvest induction protocol. As explained previously, harvesting of plants or plant parts for later use does not normally kill or harm plant tissues if they are maintained in an environmentally suitable condition.

In another embodiment, a HMG2 or HMG2-derived promoter which confers pathogen-induced expression may be used to express a variety of disease resistance genes during a pathogen infection. Examples of such resistance genes include virus coat protein, anti-sense RNA or ribozyme genes for anti-virus protection (Gadani et al., 1990, Arch. Virol 115:1–21); lysozymes, cecropins, maganins, or thionins for anti-bacterial protection; or the pathogenesis-related (PR) proteins such as glucanases and chitinases for anti-fungal protection.

In a further embodiment, a HMG2 or HMG2-derived promoter which confers pest infestation-induced expression may be used to express a variety of pest resistance genes during an insect or nematode infestation. Examples of useful gene products for controlling nematodes or insects include *Bacillus thuringiensis* endotoxins, protease inhibitors, collagenases, chitinase, glucanases, lectins, glycosidases, and neurotoxins.

The HMG2 and HMG2-derived promoters have a number of characteristics that make them particularly useful for expressing pathogen and pest resistance genes. These characteristics include these promoters' very low background activity in most uninduced tissues of the plant, their rapid induction and strong activity once induced and the relatively site-specific nature of the induced response. These combined characteristics make the HMG2-controlled resistance functions highly efficient by limiting the resistance response to the time and place that such plant responses would be the most effective (i.e., the site of the pathogen or pest ingress).

In yet another embodiment, a HMG2 or HMG2-derived promoter which confers pollen-specific expression may be used to engineer male-sterile plants. A pollen-specific HMG2 or HMG2-derived promoter may be used to express gene functions that interfere with vital cellular processes such as gene expression, cell division or metabolism. Examples of such functions include RNases, DNases, anti-sense RNAs and ribozymes. The use of pollen-specific HMG2 or HMG2-derived promoters would limit the expression of such deleterious function to pollen tissue without affecting other aspects of normal plant growth development.

6.0. EXAMPLE: ISOLATION AND CHARACTERIZATION OF THE TOMATO HMG2 PROMOTER AND HMG2 GENE FUSIONS

The isolation of the tomato HMG2 promoter is described here. The disclosed approach is applicable to the isolation of homologs of the tomato HMG2 promoter from other plant species. The approach uses a gene sequence containing the coding region of a HMGR to screen a genomic library under low stringency hybridization conditions. In the present example, the probe used was a fragment containing a region of the yeast HMGR that shows a high degree of amino acid sequence conservation with the hamster HMGR. Positive clones are isolated and subcloned where necessary, and the hybridizing region is sequenced along with the flanking sequences. Sequences containing the HMG2 gene are identified based on their nucleotide sequence comparisons with known HMGR genes and their divergence from known HMG1 genes (see Park et al., 1992, Plant Mol. Biol. 20:327–331).

Promoter:reporter gene fusions are used here to localize the HMG2 promoter elements within the cloned sequence 5' upstream of the HMGR coding sequence. One goal of the analysis is to demonstrate the tissue-specificity and defense-related and post-harvest inducibility that the 2.2 kb HMG2 promoter confers on operably linked heterologous genes. The second goal of the analysis is to determine in transgenic plants the smallest 5' upstream fragment that would confer the complete array of regulatory responses of the HMG2 gene. Thus, commencing with a 2.5 kilo-base pair (kb) fragment 5' upstream of the HMG2 transcription initiation site, smaller promoter element fragments are generated using PCR leaving out incrementally larger tracts of sequences from the 5'-end of the 2.5 kb fragment. Gene fusions are constructed by ligating the 2.2 kb EcoRI/BglII fragment and each of the smaller, PCR-generated fragments to β-glucuronidase (GUS) reporter genes. The activities of the fusion genes are examined in transgenic plants to determine the location of the HMG2 promoter.

6.1. Materials and Methods

6.1.1 Plant and Fungal Material

Tomato (*Lycopersicon esculentum* cvs. Gardener and Vendor) and tobacco (*Nicotiana tabacum* cvs. Xanthi and NC95) plants were grown under greenhouse conditions. Seedlings for transformation experiments were grown axenically as described below. For elicitor treatments of suspension cultured plant cells, tomato EP7 cells were maintained in the dark in a modified MS medium. *Verticillium albo-atrum* (race 1) and *Fusarium oxysporum* (race 1), provided by Dr. Martha Mutschler (Cornell University, Ithaca, N.Y.), were maintained on 2.4% potato dextrose agar and grown in 2.4% liquid medium for cell wall isolation. Fungal elicitor, the high molecular weight material heat-released from isolated mycelial walls was obtained and quantitated as described (Ayers et al, 1976, Plant Physiol. 57:760–765). *Rhizoctonia solani* strains RS51 and R992 were provided by Dr. Charles Hagedorn (Virginia Polytechnic Institute and State University).

6.1.2. Genomic Library Screening

Recombinant clones (500,000) of a tomato genomic DNA library (*L. esculentum* cv. VFNT Cherry) constructed in lambda Charon 35 were screened by plaque hybridization. Hybridization probe was the 1.75 kb EcoRI fragment of pJR326, (provided by Dr. Jasper Rine of University of California, Berkeley, Calif.) which contains the region of *S. cerevisiae* HMG1 most highly conserved with hamster HMGR (Basson et al., 1986, Proc. Natl. Acad. Sci. USA 83:5563–5567). Initial screening was at low stringency conditions (e.g. 30% formamide, 6× SSC, 5× Denhardt solution, 0.1% SDS, 100 ug/ml salmon sperm DNA at 37° C. for 24 hours; final wash conditions were 0.2× SSC at room temperature). Plaques giving positive hybridization signals were carried through at least three rounds of purification prior to further characterization. A 7 kb HindIII fragment of one clone (designated TH29) was subcloned into the HindIII site of transcription vector pSP6/T7 (Bethesda Research Laboratories (BRL), Gaithersburg, Md.) and designated pTH295 (FIG. 3).

6.1.3. Nucleic Acid Isolation

Total DNA was isolated from tomato leaves according to the method of Draper and Scott, (Plant Genetic Transformation and Gene Expression, 1988, Eds. Draper et al, Blackwell Scientific, Palo Alto, Calif., pp211–214)). For RNA isolation, suspension cultured tomato cells treated with elicitors, healthy roots, stems, and leaves treated by wounding (cut into 1 mm slices with a razor blade and compressed with a pestle), or intact fruit at various stages of development were stored at −70° C. Total RNA was isolated from 1 to 3 g fresh weight of tissue ground in liquid nitrogen and homogenized directly in a phenol:0.1M Tris (pH 9.0) emulsion as described previously (Haffner et al., 1978, Can. J. Biochem. 56:7229–7233).

6.1.4. Hybridization Analysis

For genomic Southern analyses, 10 μg/lane total DNA was digested with restriction endonucleases, separated on 0.8% agarose gels, and transferred to Nytran membranes using conditions recommended by manufacturer (Schleicher and Schuell, Keene, N.H.). For Northern analyses, total RNA (5 to 20 μg/lane) was denatured by treatment with glyoxal prior to electrophoresis in 1.2% agarose for gel analyses or application directly to Nytran filters utilizing a slot blotting apparatus. For hybridizations aimed at revealing all members of the HMGR gene family, probes derived from the 3' end of the gene which is most highly conserved between species (Basson et al., 1988, Mol. Cell. Biol. 8:3797–3808) were used. Either the 1.5 kb EcoRI fragment of pTH295 (FIG. 3; Yang et al., 1991, Plant Cell 5:397–405) or a 486 bp HMG2 cDNA clone from this region derived from pCD1 were 32P-labeled by random-primer methods (Multi-prime Labeling System, Amersham, UK). Membranes were prehybridized overnight without labeled probe and hybridized in the presence of 32P-labeled probe for 24 to 48 hr at 42° C. in solution containing 40% formamide, 6× SSC, 5× Denhardt solution, 5 mM EDTA, 0.1% SDS, 100 μg/ml salmon sperm DNA (Sigma). Final wash conditions were 0.1× SSC, 0.1% SDS, 1 hr at room temperature. For analyses aimed at monitoring hybridization of sequences specific only for the HMG2 isogene encoded by pTH295, the 0.7 kb AvaI-EcoRI fragment encoding 5'-untranslated regions and the 5' end of the gene or a smaller 340 bp subclone derived from this fragment and lacking the upstream region was utilized. Hybridization conditions were as described above except that 50% formamide and 5× SSC were used. Following hybridization, membranes were washed (final wash used 0.1× SSC at 50° C. for 1 hr) to remove unbound label prior to X-ray film exposure.

6.1.5. HMG2 Promoter:Reporter Gene Fusions

The 2.5 kb EcoRI fragment of the HMG2-containing clone pTH295 was inserted into the EcoRI site of a Bluescript SK-vector (Stratagene) and designated pDW101 (FIG. 3).

Digestion of this vector with EcoRI and BglII releases a fragment (about 2.2 kb) which contains sequences comprising sequences encoding the first five N-terminal amino acids of the HMG2 HMGR and extending approximately 2.2 kb 5' upstream of these coding sequences. This fragment was ligated to the GUS gene at a NcoI site to create an in-frame fusion with the ATG start codon of GUS and inserted into a modified pRK290 plasmid to generate pSLJ330.1 (FIG. 8). This plasmid was constructed at the Sainsbury Laboratory, John Innes Institute (Norwich, U.K.) in collaboration with Jonathan Jones using transformation vectors provided by Dr. Jones. Subsequent HMG2 promoter constructs were inserted into plant transformation/expression vectors of the pBI series Clontech Laboratories, Inc. Palo Alto, Calif. The pSLJ and pBI plasmids containing the fusion genes were introduced in *Agrobacterium tumefaciens* strain LBA4404 (Clontech) by tri-parental matings using the helper plasmid pRK2013.

6.1.6. Sequencing of HMG2 Promoter Deletions

Progressively larger deletions from the 3' and 5' ends of the 2.5 kb promoter region of HMG2 contained in pDW101 were generated utilizing the Exonuclease III/Mung Bean Nuclease reaction kit purchased from Stratagene (La Jolla, Calif,). Double-stranded pDW101 was digested with BamHI and SacI (both of which cut in the vector portion of the plasmid), resulting in a linear piece of DNA with a 5' overhang and a 3' overhang. After phenol:CHCl$_3$ extraction to remove the restriction enzymes, the DNA was precipitated with 100% EtOH and dried. The digested DNA was then treated with 20 units Exonuclease III/μg DNA to create a segment of single-stranded DNA. Aliquots of the reaction were removed every 45 seconds and added to tubes which contained Mung Bean Nuclease buffer. Mung Bean Nuclease was then used to digest the single-stranded portion of the DNA. This process was calculated to remove approximately 300 bp for every time point. The enzymes were extracted by treatment with lithium chloride and the DNA precipitated by the addition of sodium acetate and ethanol. This process was followed by a fill-in reaction using the Klenow fragment to ensure the presence of blunt ends for subsequent ligation. The resulting plasmids were transformed into *Escherichia coli*. Double-stranded DNA sequencing was performed using Sequenase 2.0 (United States Biochemical, Cleveland, Ohio) according to protocols provided by the manufacturer. Electrophoresis was carried out on 5% HydroLink Long Ranger acrylamide gels (AT Biochem, Malvern, Pa.).

6.1.7. GUS Gene Fusions with HMG2 Promoter Deletions

Deletions in the HMG2 promoter were created using PCR methodology. The primers used (designated in FIG. 4A–4C), and the approximate size fragments obtained were: primers #22 and #18, 1000 bp; primers #20 and #18, 460 bp; primers #19 and #18, 170 bp. Primers #19, #20 and #21 generated a flanking HindIII site; primer #18 generated a flanking BamHI site. The PCR reactions contained 1.5 mM MgCl$_2$, 200 uM each dNTP, 2.5 units Taq polymerase, 1× Taq polymerase buffer, 100 ng pDW101, and approximately 40 pmol each primer. Three cycles were used: Cycle 1 (1×): 95° C.-5 min, 72° C.-5 min, 58° C.-2 min, 72° C.-15 min, with the addition of the Taq polymerase after the first 72° incubation; Cycle 2 (40×): 95° C.-1 min, 58° C.-2 min, 72° C.-3 min; Cycle 3 (1×): 72° C.-15 min. The DNA fragments generated were electrophoresed on a 1.4% agarose gel to verify the sizes. Polyacrylamide gel-purified fragments were digested with the restriction enzymes HindIII and BamHI. These fragments were then ligated into the binary vector pBI101 which had been similarly digested (FIG. 7). The resulting plasmids, pDW201, and pDW203 (NRRL Accession No.____) were transformed into *E. coli* strain DH5α and their sequences verified. The binary plasmids were introduced into Agrobacterium strain LBA4404 using tri-parental mating.

6.1.8. Transformation of Gene Constructs into Plants

The HMG2 promoter:reporter gene fusions were transformed into tobacco according to the leaf disk transformation protocol of Horsch et al. (Horsch et al., 1985, Science, 227:1229). Prior to co-cultivation with appropriately engineered *Agrobacterium tumefaciens*, leaf disks excised from axenically grown tobacco seedlings were incubated for 8 hours on sterile filter paper overlaying a lawn of cultured tobacco "nurse" cells spread on a feeder plate (modified MS medium containing Nitsch vitamins, 100 mg/L myo-inositol, 30 gm/L sucrose, 1 mg/L 2,4-D, 0.4 mg/L mg BAP, 8 gm/L agar). Co-cultivation was accomplished by submersing the leaf disks in a suspension of *A. tumefaciens* at a concentration of 1×10$^9$ cells/ml, followed by vacuum infiltration (3×1 min). The leaf disks were then returned to the nurse plates and incubated for 48 hours at 25° C. with indirect light. Disks were then transferred to selection/regeneration plates (MS salts, Nitsch vitamins, 100 mg/L myo-inositol, 20 gm/L sucrose, 2 mg/L zeatin, 4 gm /L agar) which contain carbenicillin (500 μg/ml) and appropriate antibiotic for transformation selection. Plates were returned to the growth chamber (25° C., 18 hr light). Resulting shoots were excised and transferred to rooting media (MS salts, Nitsch vitamins, 100 mg/L myo-inositol, 30 g/L sucrose, 4 gm /L agar, and IAA and kinetin at final concentrations of 10 μM and 1 μM, respectively). Rooted plantlets were then transferred to soil and moved to the greenhouse.

Transformation of tomato was performed in a similar manner with the exception of the source of tissue. Cotyledons cut from aseptically grown tomato seedlings were cut under water using a sterile scalpel into 0.5–1.0 cm explants. Explants were then incubated on feeder plates for 8 hours prior to transformation.

6.1.9. Examination of GUS Expression in Transgenic Plants

Histochemical analysis of GUS activity in transgenic plant tissues was carried out using standard techniques well known in the art. For routine analyses, plant organs or tissue sections were submerged in a solution of 1 mM X-gluc in 50 mM phosphate buffer (pH 7) and 0.1% Triton X-100. Infiltration of the substrate was facilitated by 3×1 minute vacuum infiltration. The amount of vacuum infiltration was varied based on the thickness and hardiness of the tissue to be tested. Tissue was incubated 4–12 hours at 37° C. Following development of GUS staining, leaf tissue was generally treated with ethanol (boil 2 minutes in 95% or incubate overnight in 95%) to remove chlorophyll. GUS activity was also monitored in cell-free extracts using the fluorescent substrate MUG by standard protocols (Jefferson, 1987, Plant Mol. Biol. Rep. 5:387–405). GUS activity was expressed as nmol MU/min/μg protein where protein was determined by the method of Bradford (Pierce Coomassie Plus Protein Assay Reagent) using BSA as the standard.

6.1.10 Bacterial Infection Induction of HMG2 Promoter Activity

A 5 ml culture of *Erwinia carotovora* ssp. carotovora, strain EC14, causal agent of soft rot, was grown overnight from a single colony in LB medium at 25° C. The culture was centrifuged and resuspended in 1 ml distilled water ($OD_{600}$=3.54–3.82). Leaves, 6–8 inches in length, of greenhouse grown transgenic tobacco carrying the HMG2:GUS construct were excised at the petiole and placed on water-moistened filter paper in a large petri dish. The tip of a micropipettor was used to gently wound the top surface of the leaf while depositing 2 µl of distilled water (mock inoculation) or EC14 suspension. The plates were closed and placed in a plastic container with a tightly-fitting lid (e.g. Tupperware™) that had been lined with water-saturated paper towels and incubated at 28° C. in the dark. Samples were harvested at 24 hour intervals by excising a leaf section surrounding the site of inoculation using a hole punch or cork-borer and processed for histochemical analysis as described above.

6.1.11 Fungal Infection Induction of HMG2 Promoter Activity

Seeds of transgenic tobacco were surface sterilized by soaking in 30% bleach, rinsed 4 times with sterile water and germinated in autoclaved potting mix (ProMix BX; Premier Brands, Inc, Stamford, Conn.) in 4×4 inch PlantCons (ICN Biomedicals, Inc, Irvine, Calif.). Fungal inoculations were done by placing a fungal-infested oat seed in contact with the seedling hypocotyl. *Rhizoctonia solani* strains RS51 and R992 were inoculated as agar plugs into moist, sterilized oat seed and grown for 8 days at room temperature prior to inoculation on plants. At 24 hour intervals, seedlings were removed with care taken to limit contact with leaves to minimize wounding of the seeding near the site of inoculation, and the soil removed by dipping the roots into water. The entire seedlings, 1–2 inches in length, were then processed for histochemical GUS determination as described above. Tomato seedlings grown on agar (1/10× MS salts plus 1% agar) were also inoculated with a small agar plug of plate-grown *Rhizoctonia solani*. This method of inoculation was less effective than the soil-grown seedling method because the agar medium supported vigorous fungal growth.

6.1.12 Nematode Infestation Induction of HMG2 Promoter Activity

T1 generation tomato seedlings were grown for 10 days on seed germination media (1/10× MS salts, and 10 mg/L myo-inositol, 3 gm/L sucrose, 6 gm/agarose) in 4×4 inch Plantcons. Approximately 2000 nematodes (either *Melodigyne incognita* or *M. hapla*) were applied to the top of the media; Plantcons were then placed in a 25° C. growth chamber. Seedlings were harvested at 1, 2, 3, 5, and 7 days post-inoculation by slowly pulling seedlings from the agarose, gently removing agarose from roots, and cleanly cutting top of seedling. Roots were analyzed for GUS expression histochemically.

6.1.13 Post-Harvest Wound Induction of HMG2 Promoter Activity

Leaves approximately 8 inches in length were removed from HMG2:GUS and 35S:GUS tobacco plants and were wounded by heavily scoring with a razor blade. Sections of each leaf were immediately removed, weighed, then frozen in liquid nitrogen and stored at −70° C. Additional sections of leaf were removed, weighed, and frozen at 24 and 48 hours post-harvest. Leaf extract was obtained by grinding in MUG extraction buffer (Jefferson, 1987, Plant Mol. Biol. Rep. 5:387–405) with a mortar and pestle. Protein concentrations were determined by the Bradford method. MUG assays were performed according to the method of Jefferson (Jefferson, 1987, id.); activity was expressed as nmol MU/min/µg protein.

6.1.14 Field Performance of Transgenic Plants Containing HMG2:GUS Gene Fusions Seeds of two independent transformants of each of two cultivars (Xanthi and NC-95) showing high levels of wound-inducible HMG2:GUS activity were used for initial field tests. Seedlings of transgenic tobacco carrying a 35S:GUS construct (SJL1911, FIG. 9) were also planted to use as controls. Transgenic seedlings were grown in the greenhouse for approximately 4 weeks prior to transfer to the field. Test I involved 300 plants (seven genotypes) planted (automated planter) at the Virginia Tech Southern Piedment Agricultural Experiment Station in Blackstone, Va. Test II involved 175 plants (7 genotypes) planted as a randomized block in experimental plots at Virginia Tech, Blacksburg, Va. Leaf material is harvested at various times during the growing season (including just prior to and 2 weeks following routine topping of the plants) to determine field levels of basal HMG2 promoter activity and post-harvest induction of transgene activity. HMG2:GUS expression in response to natural pathogen pressure (including, but not limited to, cyst nematodes, aphids, beetle and hornworm predation, tobacco mosaic virus) is monitored by histochemical analysis.

6.2 Results

6.2.1 HMG2 Promoter Activity

In order to delineate regulation of HMG2 expression, 2.2 kb of HMG2 upstream sequences were fused to the GUS reporter gene in plasmid pSJL330.1 and used for *Agrobacterium tumefaciens*-mediated plant transformation. More than 20 independent GUS-expressing tobacco transformants containing 1–4 copies of this construct or a 35S:GUS control construct generated by transformation with plasmid pSJL1911 (FIG. 9; provided by Dr. Jonathon Jones, John Innes Institute, Norwich, U.K.) were generated. The 35S promoter is a high-level constitutive plant promoter derived from the cauliflower mosaic virus, (Benfey et al., 1989, EMBO J. 8:2195–2202; Fang et al., 1989, Plant Cell 1:141–150).

6.2.2 Tissue Specific Activity of the HMG2 Promoter

Plants expressing the HMG2:GUS constructs provide a powerful tool for assessing tissue-specificity of HMG2 expression. Histochemical analyses of GUS activity indicated that HMG2 is expressed in unstressed plants in the hypocotyl region of seedlings (region of shoot which breaks through soil), in trichomes (plant hairs on leaf surface important in insect, pathogen-resistance, Gershenzon et al., 1992, Anal. Biochem. 200:130–138), and in pollen (FIGS. 10A–10C). Expression in these tissues could be defense-related. Previous reports have shown that some defense-related genes are elevated in pollen (Kononowicz, 1992, Plant Cell 4:513–524). However, significant levels of GUS activity in the primary root of young tomato seedlings were also observed at sites of lateral root initiation. The significance of this expression is currently unknown. It does not appear to be related to cell division because no GUS expression is found in the zone of cell division in the root tip. The activity of the HMG2:GUS constructs has also been determined in ripening fruit of transgenic tomato plants.

Fruit at various stages of development were harvested and tested for GUS activity in cell-free extracts or analyzed for tissue specificity using histochemical assays. Immature fruit (0.5 to 1.5 cm) showed no HMG2:GUS expression. However, larger fruit (3–5 cm), mature green fruit (full size but without carotenoids), breaker fruit (undergoing carotenogenesis) and fully ripe fruit showed GUS activity. Histochemical analyses identified that the GUS activity was localized primarily to the developing seeds and fruit vasculature. The fruit showed dramatic wound-inducibility of the HMG2:GUS activity. HMG2:GUS activity was also localized to the developing seeds within the seed pods of tobacco.

Distinct regulatory circuits may mediate inducible versus developmental control of HMG2 expression. During anther (organ producing male gametophyte) development in immature flowers, wounding induces high levels of GUS, but immature pollen show no activity. As pollen matures, the pollen expresses GUS but anthers no longer show wound-inducible activity.

6.2.3 Defense-Related Activity of the HMG2 Promoter

Wounding by excision or crushing triggered rapid increases in GUS activity within 1–12 hours. This response was seen in all tissues tested with the exception of the mature anthers of tobacco (discussed above). Tissues showing marked wound-induced activation of the HMG2:GUS construct include, but are not limited to, roots, hypocotyls, and leaves of tobacco and tomato seedlings; roots, stems, petioles, pedicles, all regions of expanding and mature leaves, developing fruit and pods, mature fruit and pods, and petals of mature tobacco and tomato plants.

Inoculation of seedlings or excised leaves with compatible bacterial pathogens triggered specific HMG2:GUS expression localized to the cells directly surrounding the bacterial lesion. This response was significant at 24 hours post-inoculation (the earliest time monitored) as shown in FIG. 11A. The fungal pathogen, *Rhizoctonia solani*, also triggered dramatic increases in HMG2:GGS activity (FIG. 11B, in inoculated seedlings of both tobacco and tomato. Because these widely different microbial pathogens both trigger very similar HMG2 activation events, it is likely that other bacterial and fungal pathogens will elicit a similar response. At later times during Rhizoctonia infection, the fungus had spread down the vascular system of the plants and was associated with significant HMG2:GUS activity in these tissues. This suggest that the defense-activation properties of HMG2 will function against vascular pathogens (e.g., wilt-inducing pathogens) as well.

6.2.4 Nematode Activation of the HMG2 Promoter

Transgenic plants containing the 2.2 kb HMG2 promoter fused to GUS were analyzed for GUS activity following nematode inoculation. Tomato seedlings, germinated axenically on agar medium, were inoculated by addition of second-stage juveniles of either *Meloidogyne incognita* or *M. hapla*, causal agent of root knot disease. The transgenic cultivars were susceptible to both species. Prior to inoculation and at various times following addition of juveniles, roots were removed, histochemically assayed for GUS activity, and stained for nematodes using acid fucsin. Uninoculated roots and roots at 24 and 48 hours after inoculation showed no GUS activity at root tips (the site of nematode penetration), but GUS activity was evident at the zone of lateral root initiation and at the wound site where the stem was removed. At 24 and 48 hours post-inoculation, roots containing juveniles were observed which showed no indication of GUS activity (FIG. 12A). By 72 hrs post-inoculation some roots showed low levels of GUS activity in cells adjacent and proximal (toward the stem) to the juvenile (FIG. 12B). By five days post-inoculation, high levels of GUS activity was evident surrounding nematodes that had initiated feeding (characterized by a change in nematode morphology). By days 5–7, infected root tips showed visible swelling. This galled tissue expressed extremely high levels of GUS (FIG. 12C–12E). The responses to *M. incognita* and *M. hapla* did not differ significantly. Observation of multiple roots and plant samples suggested that the onset of HMG2 activation was closely associated with the establishment of feeding behavior. This suggests that utilization of this promoter to drive expression of transgene proteins which are toxic or inhibitory to nematode development would significantly impact disease development. Both the temporal and spacial expression patterns are optimal for rapid and highly localized delivery of nematocides or nematostatic agents.

6.2.5 Activation of the HMG2 Promoter by Natural Predators

Transgenic tobacco plants grown in the field were tested for HMG2:GUS expression in response to natural predation. Leaf sections surrounding sites of localized necrosis due to insect or microbial damage were excised and tested for localized expression of HMG2:GUS. Leaf tissue that had not been damaged showed no GUS activity. However, the region immediately surrounding the lesion showed intense GUS staining (FIG. 11C). Transgenic tobacco plants were planted in Blackstone, Va. in fields known to provide high levels of disease pressure due to the tobacco cyst nematode (*Globodera tobacum* ssp. solanaceara) in order to assess HMG2 responses to natural nematode infection.

6.2.6 Dissection of HMG2 Promoter

In order to localize elements mediating defense- and tissue-specific expression, efforts were made to generate a series of 5' promoter deletions. In the central region of the HMG2 promoter, delineated in FIG. 5, are several stretches of ATs which seemed to prevent exonuclease digestion through this area. After repeated unsuccessful attempts at exonuclease strategies, an alternative strategy based on PCR was used to generate deletions of the HMG2 promoter (see FIG. 7). These truncated promoters were fused to GUS reporter genes in the plant expression plasmid pBI101 (Clontech) and introduced into tobacco. The promoter region from −981 to +110 confers both wound and microbial pathogen responses as well as trichome and pollen expression (Table 3). However, analyses of multiple independently transformed tobacco plants suggest that the levels of transgene expression driven by this promoter are less than that of promoters that are larger (e.g., to −2.2 kb) or smaller (e.g., −347 bp). This suggests that this region may contain a "silencer" and that the region upstream of 891 contains an additional enhancer-type element. All deletions, including the construct containing only 58 bp of HMG2 upstream of the transcriptional start site continue to drive transgene expression in the pollen suggesting that developmental regulation is distinct from that associated with defense.

TABLE 3

DISSECTION OF TOMATO HMG2 PROMOTER ELEMENT

| HMG2: GUS PROMOTER[a] | | INDUCED AND TISSUE EXPRESSION[b] | | | |
|---|---|---|---|---|---|
| CONSTRUCT | REGION (bp) | Wound | Pathogens[c] | Tri-chomes | Pollen |
| SLJ 330.1 | −2.3k to +118 | ++ | +++ | ++ | ++ |
| DW 203 | −891 to +125 | + | + | + | ++ |
| DW 202 | −347 to +125 | ++ | ++ | ++ | ++ |
| DW 201 | −58 to +125 | — | — | — | + |

[a]Numbering based on the transcriptional start site designated as +1. The ATG start codon begins at base 111. GUS fusions were translationally in frame and added several bases of HMG2 coding region to the N-terminus of the GUS gene.
[b]GUS phenotype assayed in multiple independently-transformed plants for each construct.
[c]Based on leaf assays following inoculation with the soft-rotting bacterium *Erwinia carotovora* ssp. *carotovora*.

6.2.7 HMG2 Cis-Regulatory Elements

Specific cis-regulatory elements within the HMG2 promoter are identified based on functional analyses and DNA-protein interactions. For example, the region between bases −58 and −347 contains one or more elements which direct strong wound and pathogen induction. The −58 to −347 fragment is generated by PCR using primer 21 and a primer complementary to primer 19 (see FIG. 4A–4C). Additional 3' and 5' oligonucleotide primers synthesized based on sequences within this region will generate subfragments for analyses of regulatory activity. Functional analyses entail fusion of these fragments to appropriate "minimal" plant promoters fused to a reporter gene such as the minimal 35S promoter (discussed in Sections 5.2 and 5.3, above) and introduction and expression of the resulting constructs in plants or plant cells. Regions containing fully-functional HMG2 cis-regulatory elements will confer HMG2-specific regulation on this minimal promoter as determined by wound-, pathogen-, pest-, or elicitor-inducibility or generation of HMG2 sequence-dependent developmental patterns of GUS expression. Specific cis-regulatory elements are further delineated by gel shift or footprint/DNase sensitivity assays. The −58 to −347 fragment or other HMG2 promoter fragments, generated by PCR amplification, are incubated with nuclear extracts from control and defense-elicited cells. For example, nuclei are isolated (Elliot et al., 1985, Plant Cell 1:681–690) from untreated tomato suspension cultured cells and cells 6–8 hours after treatment with fungal elicitor or arachidonic acid (Park, 1990, *Lycopersican esculentum* Mill., Ph.D. Dissertation, Virginia Polytechnic Institute and State University; Yang et al., 1991, Plant Cell 3:397–405). PCR fragments which interact with nuclear components are identified based on reduced mobility in polyacrylamide gel electrophoresis or by digestion with DNase I and analysis of DNase-insensitive areas on sequencing gels. Defense-responsive elements may or may not demonstrate differential patterns upon interaction with control versus elicitor-treated extracts. Promoter regions identified as having DNA-protein interactions are further tested by creating chimeric constructs with, for example, "minimal" 35S promoters to determine effects of the cis-regulatory element on heterologous gene expression in transgenic plants or plant cells. This strategy may separate specific HMG2 promoter functions (e.g., wound from pathogen induction, or defense from developmental regulation) and delineate additional or novel uses of HMG2 promoter elements.

6.2.8 Post-Harvest Induction of HMG2 Promoter

An important use of the current invention is to facilitate the production of valuable proteins in transgenic plants. This promoter is particularly useful in this capacity in that it is highly inducible in plant tissues following harvest. The yield of a specific transgene, β-glucuronidase (GUS), was compared for transgenic plants containing the HMG2:GUS construct versus those containing a 35S:GUS construct. The 35S promoter from the cauliflower mosaic virus is widely used in transgenic plant research because it directs high levels of transgene expression in most tissues (Benfey et al., 1989, EMBO J. 8:2195–2202). Leaf material was harvested from greenhouse-grown plants and wounded by scoring with a razor blade. Tissue was extracted for GUS activity immediately after harvest/wounding and after 24 and 48 hours of room temperature storage in zip-lock bags to prevent desiccation. The leaves containing the 35S:GUS construct showed greater than 50% loss of GUS activity within 24 hours of harvest. For industrial utilization of transgenic tobacco for bioproduction of a high-value protein, this loss would be highly significant. In contrast, the HMG2:GUS construct was less active immediately after harvest, but by 48 hours, directed wound-induced transgene product accumulation to levels comparable to pre-storage 35S:GUS levels.

A transgenic plant carrying a heterologous gene encoding a valuable product, for example a human therapeutic protein of pharmaceutical value, fused to the HMG2 promoter would be expressed at relatively low levels throughout the growing cycle of a transgenic plant (e.g., tobacco). Thus, transgene expression is unlikely to affect biomass yield. Upon optimal biomass production, the plants are harvested (e.g., by mowing) and the leaf material is transferred to the laboratory or processing facility. HMG2-driven heterologous gene expression is triggered by mechanical wounding or wounding plus chemical or elicitor treatment and the transgene product is then recovered for further processing accumulation. The time range of product accumulation is generally (but not limited to) 24 to 72 hours depending on the time and conditions between harvest and induction and the stability properties of the specific heterologous gene product.

Heterologous gene products whose production or high-level accumulation is deleterious to the growth or vigor of the plant can similarly be produced by utilizing the post-harvest induction characteristics of the HMG2 promoter. For highly toxic products it is advantageous to further dissect the promoter to minimize developmental expression but retain the wound and elicitor inducible responses. Promoter deletion analyses (Table 3) indicate that multiple cis-regulatory elements are present in the promoter and that the developmental functions (e.g., pollen) are separable from the defense-specific functions (e.g., wound, pathogen responses). These analyses indicate that the wound and pathogen response elements are distal to those elements mediating pollen expression.

6.2.9. Use of HMG2 Promoter for Developing Nematode Resistant Plants

Another important use of the present invention is the development of nematode-resistant plants. Such resistant plants are developed by using a HMG2 promoter element to control the expression of a heterologous gene which is or whose product is toxic or inhibitory to nematodes. Key advantages of using the HMG2 expression systems for this purpose are that 1) the heterologous gene product will be limited primarily to tissues undergoing disease-related stress, and 2) the heterologous gene will be strongly activated directly in the tissue of ingress, thus delivering a significant "dose" to the nematode.

The coding region of potato proteinase inhibitor I or II (Johnson et al., 1989, Proc. Natl. Acad. Sci. USA 86:9871–9875) is excised by appropriate restriction enzymes and inserted into a plant expression vector downstream of the HMG2 promoter or a chimeric promoter containing active cis-regulatory element(s) of the HMG2 promoter. Appropriate enzyme sites or linker fragments are used to assure correct positioning of the coding region with the transcriptional and translational initiation sites. The plasmid pDW202 (FIG. 7) is digested with SmaI and SstI and gel purified to obtain the vector/HMG2 promoter fragment separate from the fragment containing the excised GUS coding region. The appropriately digested and processed potato proteinase inhibitor I gene is then ligated into the SmaI/SstI site. The resulting plasmid is transformed into E. coli strain DH5α and sequenced to assure correct insertion and orientation prior to introduction into Agrobacterium strain LBA4404 by triparental mating. The engineered LBA4404 is then used for tobacco leaf disk co-cultivation and the transformed tobacco is subsequently regenerated to mature plants.

Enzymatic or immuno-detection of proteinase inhibitor I in transgenic plants is done by described methods (Johnson et al., 1989, Proc. Natl. Acad. Sci. USA 86:9871–9875). The effect of the introduced HMG2:Proteinase inhibitor constructs on plant:nematode interactions is tested in seedlings inoculated, for example, with root knot (*Meloidogyne incognita, M. halpa*) or cyst (*Globodera tobacum*) nematodes or by planting seedlings in fields of known disease pressure. Plants are monitored for overall health, number of feeding female nematodes, number and severity of galls, and nematode egg production.

In another strategy, HMG2 promoter-driven expression of an anti-sense RNA may be used to block production of plant compounds required by parasitic nematodes. For instance, root knot and cyst nematodes are dependent upon plant sterols for growth and reproduction. Thus, sequences from the tomato HMG1 (sterol-specific) isogene (e.g., regions with the N-terminus specific for HMG1 and not other HMGR isogenes) or the tomato squalene synthetase gene are introduced into the SmaI/SstI digested vector described above such that the complementary RNA strand is produced. Expression of these gene constructs in transgenic tomato decrease or block sterol production in plant cells where HMG2 promoter is active and thus reduce or prevent nematode growth and development.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publication are cited herein, the disclosure of which are incorporated by reference in their entireties.

What is claimed is:

1. An isolated HMG2 promoter comprising a promoter of a plant gene whose coding sequence selectively hybridizes under high stringency conditions to a tomato 3-hydroxy-3-methylglutaryl CoA reductase 2 (HMGR2) coding sequence, which HMG2 promoter confers wound-induced, pathogen infection-induced, pest infestation-induced or elicitor-induced expression to an operably linked coding sequence.

2. The isolated HMG2 promoter according to claim 1, wherein the HMG2 promoter is a tomato HMG2 promoter.

3. The isolated HMG2 promoter according to claim 2, wherein the HMG2 promoter comprises the 2.2 kb EcoRI-BglII restriction fragment of pDW101.

4. The isolated HMG2 promoter according to claim 2, wherein the HMG2 promoter comprises the 0.46 kb HindIII-BamHI restriction fragment of pDW202.

5. The isolated HMG2 promoter according to claim 2, wherein the HMG2 promoter comprises the 1.0 kb HindIII-BamHI restriction fragment of pDW203.

6. A gene fusion comprising the HMG2 promoter of claim 1 operably linked to a second nucleotide sequence encoding a heterologous gene, wherein the transcription of the heterologous gene is under the control of the HMG2 promoter.

7. The gene fusion according to claim 6, wherein the HMG2 promoter is a tomato HMG2 promoter.

8. The gene fusion according to claim 7, wherein the HMG2 promoter comprises the 2.2 kb EcoRI-BglII restriction fragment of pDW101.

9. The gene fusion according to claim 7, wherein the HMG2 promoter comprises the 0.17 kb HindIII-BamHI restriction fragment of pDW201.

10. The gene fusion according to claim 7, wherein the HMG2 promoter comprises the 0.46 kb HindIII-BamHI restriction fragment of pDW302.

11. The gene fusion according to claim 7, wherein the HMG2 promoter comprises the 1.0 kb HindIII-BamHI restriction fragment of pDW203.

12. A chimeric promoter comprising a plant promoter or truncated promoter ligated to a cis-regulatory element of the HMG2 promoter of claim 1, wherein i) the truncated promoter comprises a sequence whose 3'-end is at the nucleotide corresponding to the transcription initiation site of said truncated promoter and whose 5'-end is at a nucleotide 46 to 150 bases 5' upstream of said 3'-end, and which truncated promoter is not derived from the HMG2 promoter, ii) the cis-regulatory element of the HMG2 is ligated 5' upstream of the truncated promoter or within the regulatory region of the plant promoter, and iii) the cis-regulatory element of the HMG2 promoter confers wound-induced, pathogen infection-induced, pest infestation-induced or elicitor-induced transcriptional activity to the chimeric promoter.

13. The chimeric promoter of claim 12, wherein the HMG2 promoter is a tomato HMG2 promoter.

14. The chimeric promoter of claim 13, wherein the cis-regulatory element comprises the tomato HMG2 promoter sequence depicted in FIGS. 4A–4C (SEQ ID NO:3) from nucleotide residue number −35 to −1,036.

15. The chimeric promoter of claim 13, wherein the cis-regulatory element comprises the 480 bp tomato HMG2 promoter sequence depicted in FIG. 5 (SEQ ID NO:4).

16. The chimeric promoter of claim 13, wherein the cis-regulatory element comprises the 515 bp sequence depicted in FIG. 6 (SEQ ID NO:5).

17. A gene fusion comprising the chimeric promoter of claim 12 operably linked to a second nucleotide sequence encoding a heterologous gene, wherein the transcription of the gene is under the control of said chimeric promoter.

18. A gene fusion comprising the chimeric promoter of claim 13 operably linked to a second nucleotide sequence encoding a heterologous gene, wherein the transcription of the gene is under the control of said chimeric promoter.

19. A gene fusion comprising the chimeric promoter of claim 14 operably linked to a second nucleotide sequence encoding a heterologous gene, wherein the transcription of the gene is under the control of said chimeric promoter.

20. A gene fusion comprising the chimeric promoter of claim 15 operably linked to a second nucleotide sequence encoding a heterologous gene, wherein the transcription of the gene is under the control of said chimeric promoter.

21. A gene fusion comprising the chimeric promoter of claim 16 operably linked to a second nucleotide sequence encoding a heterologous gene, wherein the transcription of the gene is under the control of said chimeric promoter.

22. A recombinant DNA vector having the gene fusion of any one of claims 6 to 11 and 17 to 21.

23. A plant cell having the gene fusion of any one of claims 6 to 11 and 17 to 21.

24. A plant having the gene fusion of any one of claims 6 to 11 and 17 to 21.

25. A method for producing a product encoded by a heterologous gene in a plant cell, comprising cultivating the plant cell of claim 23; including the expression of the gene fusion in the plant cell by wounding, elicitor treatment, pathogen infection or pest infestation; and recovering the expressed heterologous gene product from the plant cell.

26. A method for producing a product encoded by a heterologous gene in a plant, comprising growing the plant of claim 24; including the expression of the gene fusion in the plant by wounding, elicitor treatment, pathogen infection, or pest infestation; harvesting the plant; and processing the harvested plant for use or extracting the expressed heterologous gene product from the harvested plant.

27. The method of 26, wherein the expression of the gene fusion is induced immediately prior to, during or immediately after harvesting the plant.

28. The plant of claim 24, wherein the heterologous gene of said gene fusion encodes a microbial disease resistance gene.

29. The plant of claim 24, wherein the heterologous gene of said gene fusion encodes a pest resistance gene.

30. An isolated HMG2 promoter which is a DNA selected from the group consisting of a) the 2.2 kb EcoRI-BglII restriction fragment of pDW101, b) the 0.46 kb HindIII-BamHI restriction fragment of pDW202, and c) the 1.0 kb HindIII-BamHI restriction fragment of pDW203.

* * * * *